(12) United States Patent
Casas

(10) Patent No.: US 10,951,872 B2
(45) Date of Patent: *Mar. 16, 2021

(54) AUGMENTED REALITY GUIDANCE FOR SPINAL PROCEDURES USING STEREOSCOPIC OPTICAL SEE-THROUGH HEAD MOUNTED DISPLAYS WITH REAL TIME VISUALIZATION OF TRACKED INSTRUMENTS

(71) Applicant: OnPoint Medical, Inc., Bedford, MA (US)

(72) Inventor: Carlos Quiles Casas, Badajoz (ES)

(73) Assignee: OnPoint Medical, Inc., Bedford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/065,911

(22) Filed: Oct. 8, 2020

(65) Prior Publication Data

US 2021/0037224 A1 Feb. 4, 2021

Related U.S. Application Data

(63) Continuation of application No. 16/919,639, filed on Jul. 2, 2020, now Pat. No. 10,841,556, which is a
(Continued)

(51) Int. Cl.
*H04N 13/00* (2018.01)
*H04N 13/111* (2018.01)
(Continued)

(52) U.S. Cl.
CPC ............ *H04N 13/111* (2018.05); *A61B 34/10* (2016.02); *A61B 34/20* (2016.02);
(Continued)

(58) Field of Classification Search
CPC ......... A61B 6/5247; A61B 1/00; A61B 90/36; A61B 2090/365; A61B 34/00; G06F 19/00; H04N 7/00; H04N 13/00; G06T 19/00
See application file for complete search history.

(56) References Cited

U.S. PATENT DOCUMENTS 5,526,812 A   6/1996   Dumoulin et al.
5,676,673 A   10/1997  Ferre et al.
(Continued)

FOREIGN PATENT DOCUMENTS

EP   1028659 B1   2/2004
GB   2498833 B    12/2016
(Continued)

OTHER PUBLICATIONS

Abe et al., "A Novel 3D Guidance System Using Augmented Reality for Percutaneous Vertebroplasty", Journal of Neurological Spine, vol. 19, pp. 492-501, Oct. 2013.
(Continued)

*Primary Examiner* — Maryam A Nasri
(74) *Attorney, Agent, or Firm* — Greenberg Traurig, LLP; Natalie Salem; Barry Schindler

(57) ABSTRACT

Embodiments disclose a real-time surgery method and apparatus for displaying a stereoscopic augmented view of a patient from a static or dynamic viewpoint of the surgeon, which employs real-time three-dimensional surface reconstruction for preoperative and intraoperative image registration. Stereoscopic cameras provide real-time images of the scene including the patient. A stereoscopic video display is used by the surgeon, who sees a graphical representation of the preoperative or intraoperative images blended with the video images in a stereoscopic manner through a see-through display.

30 Claims, 6 Drawing Sheets

Related U.S. Application Data continuation of application No. 16/822,062, filed on Mar. 18, 2020, now Pat. No. 10,742,949, which is a continuation of application No. 16/598,697, filed on Oct. 10, 2019, now Pat. No. 10,602,114, which is a continuation of application No. 16/518,426, filed on Jul. 22, 2019, now Pat. No. 10,511,822, which is a continuation of application No. 16/240,937, filed on Jan. 7, 2019, now abandoned, which is a continuation of application No. 15/972,649, filed on May 7, 2018, now Pat. No. 10,194,131, which is a continuation of application No. 14/753,705, filed on Jun. 29, 2015, now Pat. No. 10,154,239.

(60) Provisional application No. 62/097,771, filed on Dec. 30, 2014.

(51) Int. Cl.

| | | |
|---|---|---|
| *G06T 19/00* | (2011.01) | |
| *A61B 34/20* | (2016.01) | |
| *A61B 34/10* | (2016.01) | |
| *H04N 13/156* | (2018.01) | |
| *H04N 13/296* | (2018.01) | |
| *G06F 3/01* | (2006.01) | |
| *H04N 13/279* | (2018.01) | |
| *H04N 13/239* | (2018.01) | |
| *G06F 3/03* | (2006.01) | |
| *G06F 3/0484* | (2013.01) | |
| *H04N 13/366* | (2018.01) | |
| *G02B 27/01* | (2006.01) | |
| *A61B 90/00* | (2016.01) | |
| *A61B 1/00* | (2006.01) | |

(52) U.S. Cl.
CPC .......... *G02B 27/0172* (2013.01); *G06F 3/011* (2013.01); *G06F 3/017* (2013.01); *G06F 3/0304* (2013.01); *G06F 3/04845* (2013.01); *G06T 19/006* (2013.01); *H04N 13/156* (2018.05); *H04N 13/239* (2018.05); *H04N 13/279* (2018.05); *H04N 13/296* (2018.05); *H04N 13/366* (2018.05); *A61B 1/00* (2013.01); *A61B 2034/2057* (2016.02); *A61B 2034/2065* (2016.02); *A61B 2090/371* (2016.02); *G02B 2027/014* (2013.01); *G02B 2027/0134* (2013.01); *G02B 2027/0138* (2013.01); *G06F 2203/04804* (2013.01); *G06T 2210/41* (2013.01)

(56) References Cited

U.S. PATENT DOCUMENTS

| | | | |
|---|---|---|---|
| 5,800,352 | A | 9/1998 | Ferre et al. |
| 5,803,089 | A | 9/1998 | Ferre et al. |
| 5,829,444 | A | 11/1998 | Ferre et al. |
| 5,873,822 | A | 2/1999 | Ferre et al. |
| D415,146 | S | 10/1999 | Hori |
| 5,967,980 | A | 10/1999 | Ferre et al. |
| 6,175,756 | B1 | 1/2001 | Ferre et al. |
| 6,341,231 | B1 | 1/2002 | Ferre et al. |
| 6,396,497 | B1 | 5/2002 | Reichlen |
| 6,445,943 | B1 | 9/2002 | Ferre et al. |
| 6,599,247 | B1 | 7/2003 | Stetten |
| 6,714,810 | B2 | 3/2004 | Grzeszczuk et al. |
| 7,130,676 | B2 | 10/2006 | Barrick |
| 7,774,044 | B2 | 8/2010 | Sauer et al. |
| 7,812,815 | B2 | 10/2010 | Banerjee et al. |
| 8,320,612 | B2 | 11/2012 | Knobel et al. |
| 8,730,266 | B2 | 5/2014 | Brown et al. |
| 8,989,843 | B2 | 3/2015 | Chien |
| 9,068,820 | B2 | 6/2015 | Kosmecki et al. |
| 9,068,824 | B2 | 6/2015 | Findeisen et al. |
| 9,123,155 | B2 | 9/2015 | Cunningham et al. |
| 9,183,560 | B2 | 11/2015 | Abelow |
| 9,215,293 | B2 | 12/2015 | Miller |
| 9,299,138 | B2 | 3/2016 | Zellner et al. |
| 9,310,559 | B2 | 4/2016 | Macnamara |
| 9,311,284 | B2 | 4/2016 | Warila et al. |
| 9,389,424 | B1 | 7/2016 | Schowengerdt |
| 9,417,452 | B2 | 8/2016 | Schowengerdt et al. |
| 9,429,752 | B2 | 8/2016 | Schowengerdt et al. |
| 9,503,681 | B1 | 11/2016 | Popescu et al. |
| 9,547,940 | B1 | 1/2017 | Yu et al. |
| 9,582,717 | B2 | 2/2017 | Lee et al. |
| 9,792,721 | B2 | 10/2017 | Kosmecki et al. |
| 9,858,721 | B2* | 1/2018 | Maimone .............. G06T 19/006 |
| 9,901,463 | B2 | 2/2018 | Mahfouz |
| 9,913,692 | B2 | 3/2018 | Arata et al. |
| 9,918,658 | B2 | 3/2018 | McCaulley et al. |
| 9,983,412 | B1* | 5/2018 | Fuchs ................ G02B 27/0172 |
| 10,154,239 | B2 | 12/2018 | Casas |
| 10,194,131 | B2 | 1/2019 | Casas |
| 10,326,975 | B2 | 6/2019 | Casas |
| 10,511,822 | B2 | 12/2019 | Casas |
| 10,594,998 | B1 | 3/2020 | Casas |
| 10,602,114 | B2 | 3/2020 | Casas |
| 10,742,949 | B2 | 8/2020 | Casas |
| 2001/0041838 | A1 | 11/2001 | Holupka et al. |
| 2002/0082498 | A1 | 6/2002 | Wendt et al. |
| 2002/0163499 | A1 | 11/2002 | Sauer |
| 2005/0113846 | A1 | 5/2005 | Carson |
| 2005/0215879 | A1 | 9/2005 | Chuanggui |
| 2005/0267353 | A1 | 12/2005 | Marquart et al. |
| 2005/0281465 | A1 | 12/2005 | Marquart et al. |
| 2006/0142739 | A1 | 6/2006 | DiSilestro et al. |
| 2007/0015999 | A1 | 1/2007 | Heldreth et al. |
| 2007/0035511 | A1 | 2/2007 | Banerjee et al. |
| 2007/0038944 | A1 | 2/2007 | Carignano et al. |
| 2007/0236514 | A1 | 10/2007 | Agusanto et al. |
| 2007/0276234 | A1 | 11/2007 | Shahidi |
| 2009/0068620 | A1 | 3/2009 | Knobel et al. |
| 2009/0089081 | A1 | 4/2009 | Haddad |
| 2009/0138019 | A1 | 5/2009 | Wasielewski |
| 2009/0267805 | A1 | 10/2009 | Jin et al. |
| 2011/0190637 | A1 | 8/2011 | Knobel et al. |
| 2013/0261633 | A1 | 3/2013 | Thornberry |
| 2013/0093829 | A1 | 4/2013 | Rosenblatt et al. |
| 2013/0096373 | A1 | 4/2013 | Chabanas et al. |
| 2013/0116574 | A1 | 5/2013 | Knobel et al. |
| 2013/0169683 | A1 | 7/2013 | Perez et al. |
| 2013/0261503 | A1 | 10/2013 | Sherman et al. |
| 2013/0261504 | A1 | 10/2013 | Claypool et al. |
| 2013/0296682 | A1 | 11/2013 | Clavin et al. |
| 2013/0326364 | A1 | 12/2013 | Latta et al. |
| 2014/0081659 | A1 | 3/2014 | Nawana et al. |
| 2014/0085203 | A1 | 3/2014 | Kobayashi |
| 2014/0088941 | A1 | 3/2014 | Banerjee et al. |
| 2014/0118335 | A1 | 5/2014 | Gurman |
| 2014/0135746 | A1 | 5/2014 | Scheopp |
| 2014/0198190 | A1 | 7/2014 | Okumu |
| 2014/0218366 | A1 | 8/2014 | Kosmecki et al. |
| 2014/0275760 | A1 | 9/2014 | Lee et al. |
| 2014/0303491 | A1 | 10/2014 | Shekhar et al. |
| 2014/0334670 | A1 | 11/2014 | Guigues et al. |
| 2015/0045657 | A1* | 2/2015 | Kim ...................... A61B 6/032 |
| | | | 600/424 |
| 2015/0100067 | A1 | 4/2015 | Cavanagh et al. |
| 2015/0206218 | A1 | 7/2015 | Banerjee et al. |
| 2015/0366628 | A1 | 12/2015 | Ingmanson |
| 2016/0163105 | A1 | 6/2016 | Hong et al. |
| 2016/0182877 | A1 | 6/2016 | Deluca |
| 2016/0191887 | A1 | 6/2016 | Casas |
| 2016/0206379 | A1 | 7/2016 | Flett et al. |
| 2016/0220105 | A1 | 8/2016 | Duret |
| 2016/0225192 | A1 | 8/2016 | Jones et al. |
| 2016/0228193 | A1 | 8/2016 | Moctezuma De La Barrera et al. |
| 2016/0287337 | A1 | 10/2016 | Aram et al. |
| 2016/0324580 | A1 | 11/2016 | Esterberg |
| 2016/0381256 | A1 | 12/2016 | Aguirre-valencia |

(56) References Cited

U.S. PATENT DOCUMENTS

| | | |
|---|---|---|
| 2017/0027651 A1 | 2/2017 | Esterberg |
| 2017/0035517 A1 | 2/2017 | Geri et al. |
| 2017/0071673 A1 | 3/2017 | Ferro et al. |
| 2017/0108930 A1 | 4/2017 | Banerjee et al. |
| 2017/0160549 A1 | 6/2017 | Badiali et al. |
| 2017/0178375 A1 | 6/2017 | Benishti et al. |
| 2017/0202633 A1 | 7/2017 | Liu |
| 2017/0231714 A1 | 8/2017 | Kosmecki et al. |
| 2017/0231715 A1* | 8/2017 | Roger ............... A61B 17/7032 600/424 |
| 2018/0262743 A1 | 9/2018 | Casas |
| 2019/0149797 A1 | 5/2019 | Casas |
| 2019/0216452 A1 | 7/2019 | Nawana et al. |
| 2019/0246088 A1 | 8/2019 | Casas |
| 2019/0349559 A1 | 11/2019 | Casas |
| 2020/0053335 A1 | 2/2020 | Casas |

FOREIGN PATENT DOCUMENTS

| | | |
|---|---|---|
| WO | 1993025157 A1 | 12/1993 |
| WO | 2005088539 A2 | 9/2005 |
| WO | 2010/034117 A1 | 4/2010 |
| WO | 2014057352 A1 | 4/2014 |
| WO | 2015/110859 A1 | 7/2015 |
| WO | 2015145395 A1 | 10/2015 |
| WO | 2016028828 A1 | 2/2016 |
| WO | 2016162789 A2 | 10/2016 |
| WO | 2016195401 A1 | 12/2016 |
| WO | 2016207628 A1 | 12/2016 |

OTHER PUBLICATIONS

Bauer, Sebastian, Doctoral Thesis, "Rigid and Non-Rigid Surface Registration for Range Imaging Applications in Medicine", urn:nbn:de:bvb:29-opus4-54665, Nov. 27, 2014.

Bauer et al., "Multi-Modal Surface Registration for Markerless Initial Patient Setup in Radiation Therapy Using Microsoft's Kinect Sensor", 2011 IEEE International Conference on Computer Vision Workshops (ICCV Workshops), Barcelona, Nov. 2011, pp. 1175-1181, Jan. 16, 2012.

Ferrari et al., "Video See-Through in the Clinical Practice", 1st International Workshop on Engineering Interactive Computing Systems for Medicine and Health Care, EICS4Med. vol. 727, pp. 19-24, 2011.

Hayashibe et al., "Surgical Navigation Display System Using Volume Rendering of Intraoperatively Scanned CT Images", Computer Aided Surgery, vol. 11, No. 5, pp. 240-246, Sep. 2006.

Jiang et al., "A Robust Automated Markerless Registration Framework for Neurosurgery Navigation", The International Journal of Medical Robotics and Computer Assisted Surgery, vol. 11, pp. 436-447, Oct. 19, 2014.

Kersten-Oertel et al., "The State of the Art of Visualization in Mixed Reality Image Guided Surgery", Computerized Medical Imaging and Graphics, vol. 37, pp. 98-112, Jan. 2013.

Kutter et al., "Real-time Volume Rendering for High Quality Visualization in Augmented Reality", International Workshop on Augmented Environments for Medical Imaging including Augmented Reality in Computer-aided Surgery (AMI-ARCS 2008), New York, MICCAI Society, Sep. 2008.

Maier-Hein et al., "Optical Techniques for 3D Surface Reconstruction in Computer-Assisted Laparoscopic Surgery", Medical Image Analysis, vol. 17, pp. 974-996, May 3, 2013.

Muller et al., "Automatic Multi-Modal ToF/CT Organ Surface Registration", Bildverarbeitung für die Medizin, pp. 154-158, Mar. 2011.

Noonan et al., "The Design and Initial Calibration of an Optical Tracking System Using the Microsoft Kinect", IEEE Nuclear Science Symposium Conference Record, pp. 3614-3617, Oct. 2011.

Pauly et al., "Machine Learning-Based Augmented Reality for Improved Surgical Scene Understanding", Computerized Medical Imaging and Graphics, vol. 1280, pp. 1-6, Jun. 2014.

Ren et al., "Marker-Based Surgical Instrument Tracking Using Dual Kinect Sensors", IEEE Transactions on Automation Science and Engineering, vol. 11, No. 3, pp. 921-924, Jul. 2014.

Vagvolgyi et al., "Video to CT Registration for Image Overlay on Solid Organs", Procedural Augmented Reality in Medical Imaging and Augmented Reality in Computer-Aided Surgery (AMIARCS) pp. 78-86, 2008.

Wang et al., "Augmented Reality Navigation with Automatic Marker-Free Image Registration Using 3-D Image Overlay for Dental Surgery", IEEE Transactions on Biomedical Engineering, vol. 61, No. 4, pp. 1295-1304, Apr. 2014.

Ye et al., "Accurate 3D Pose Estimation From a Single Depth Image", IEEE International Conference on Computer Vision (ICCV), pp. 731-738, Nov. 2011.

Lamata et al., "Augmented Reality for Minimally Invasive Surgery: Overview and Some Recent Advances", Augmented Reality, Jan. 2010, pp. 230, INTECH, Croatia.

Liao et al., "Surgical Navigation by Autostereoscopic Image verlay of Integral Videography", IEEE Transactions on Information Technology in Biomedicine, Jun. 2004, p. 114-121, vol. 8, No. 2, IEEE.

Lievin and Keeve, "Stereoscopic Augmented Reality System for Computer Assisted Surgery", CARS, Jun. 27-30, 2001, Berlin, Germany.

Lindert et al., "The Use of a Head-Mounted Display for Visualization in Neuroendoscopy", Computer Aided Surgery, 2004, 9:6, 251-256, Taylor & Francis Group.

Linte et al., "On Mixed Reality Environments for Minimally Invasive Therapy Guidance: Systems Architecture, Successes and Challenges in Their Implementation from Laboratory to Clinic", Comput Med Imaging Graph, Mar. 2013, 37(2):83-97.

Lorensen and Cline, "Marching Cubes: A High Resolution 3D Surface Construction Algorithm", Computer Graphics, Jul. 1987, p. 163-169, vol. 21, No. 4, Schenectady, New York.

Liu et al., "An Optical See-Through Head Mounted Display with Addressable Focal Planes", IEEE International Symposium on Mixed and Augmented Reality, Sep. 15-18, 2008, p. 33-42.

Masamune et al., "An Image Overlay System with Enhanced Reality for Percutaneous Therapy Performed Inside CT Scanner", MICCAI, 2002, pp. 77-84, LNCS 2489, Springer-Verlag Berlin Heidelberg.

Maurer et al., "Augmented Reality Visualization of Brain Structures with Stereo and Kinetic Depth Cues: System Description and Initial Evaluation with Head Phantom", Medical Imaging 2001: Visualization, Display, and Image-Guided Procedures, Feb. 17-22, 2001, pp. 445-456, Society of Photo-Optical Instrumentation Engineers.

Melzer, "Head-Mounted Displays", The Avionics Handbook, 2001, CRC Press LLC.

Menozzi et al., "Development of Vision-Aided Navigation for a Wearable Outdoor Augmented Reality System", IEEE, 2014, 760-772.

MicroVision, 2015 Annual Report.

"Microvision's Nomad Augmented Vision System: The How and the Why", SID Pacific Northwest Chapter Meeting, Jun. 11, 2003.

Moore et al., "Image Guidance for Spinal Facet Injections Using Tracked Ultrasound", MICCAI, 2009, pp. 516-523, Part I, LNCS 5761, Springer-Verlag Berlin Heidelberg.

Newcombe et al., "KinectFusion: Real-Time Dense Surface Mapping and Tracking", IEEE ISMAR, Inproceedings, 2011.

Nikou et al., "Augmented Reality Imaging Technology for Orthopaedic Surgery", Operative Techniques in Orthopaedics, Jan. 2000, pp. 82-86, vol. 10, No. 1.

Okamura, "Lecture 8: Tracking and Surgical Navigation, Registration", ME 328: Medical Robotics, Spring 2013.

Ortega et al., "Usefulness of a Head Mounted Monitor Device for Viewing Intraoperative Fluoroscopy During Orthopaedic Procedures", Arch Orthop Trauma Surg, 2008, 128:1123-1126, Springer-Verlag.

Paprosky et al., "Intellijoint HIP: a 3D Mini-Optical Navigation Tool for Improving Intraoperative Accuracy During Total Hip Arthroplasty", Med Devices, 2016, 9: 401-408, Dove Medical Press Limited.

Peters et al., "Image Guided Interventions: Technology and Applications", 2008, Springer Science + Business Media, LLC.

(56) References Cited

OTHER PUBLICATIONS

Ponce et al., "Emerging Technology in Surgical Education: Combining Real-Time Augmented reality and Wearable Computing Devices", The Cutting Edge, Nov. 2014, pp. 751-757, vol. 37, No. 11.
Qian et al., "Comprehensive Tracker Based Display Calibration for Holographic Optical See-Through Head-Mounted Display", 2017.
Rhodes, "A Brief History of Wearable Computing", http://wearables.www.media.mit.edu/projects/wearables/timeline.html.
Rinaldi et al., "Computer-Guided Applications for Dental Implants, Bone Grafting, and Reconstructive Surgery", 2009, Elsevier.
Robinett et al., "A Computer Model for the Stereoscopic Optics of a Head-Mounted Display", SPIE, vol. 1457, Stereoscopic Displays and Applications II, 1991.
Rolland et al., "A Comparison of Optical and Video See-Through Head-Mounted Displays", SPIE, vol. 2351, Telemanipulator and Telepresence Technologies, 1994.
Rolland et al., "Optical Versus Video See-Through Head-Mounted Displays in Medical Visualization", Presence, vol. 9, No. 3, pp. 287-309, Jun. 2000.
Rosenthal et al., "Augmented Reality Guidance for Needle Biopsies: A Randomized, Controlled Trial in Phantoms", MICCAI, 2001, LNCS 2208: 240-248.
Rosman et al., "Articulated Motion Segmentation of Point Clouds by Group-Valued Regularization", Eurographics Workshop on 3D Object Retrieval, 2012.
Sauer et al., "An Augmented Reality Navigation System with a Single-Camera Tracker: System Design and Needle Biopsy Phantom Trial", MICCAI, 2002, LNCS 2489: 116-124.
Sauer et al., "Augmented Workspace: Designing an AR Testbed", IEEE, 2000, 47-53.
Scuderi et al.,"Total Knee Arthroplasty with a Novel Navigation System Within the Surgical Field", Orthop Clin N Am 45, 2014, 167-173, Elsevier.
Vogt, "Real-Time Augmented Reality for Image-Guided Interventions", 2009, Erlangen-Nurnberg.
Shen et al., "3D Augmented Reality with Integral Imaging Display", SPIE vol. 9867, Three-Dimensional Imaging, Visualization,and Display, 2016.
Liao et al., "3-D Augmented Reality for MRI-Guided Surgery Using Integral Videography Autostereoscopic Image Overlay", IEEE 2010.
Sherstyuk et al., "Dynamic Eye Convergence for Head-Mounted Displays Improves User Performance in Virtual Environments", the Association for Computing Machinery, Inc., 2012.
State et al., "Stereo magery from the UNC Augmented Reality System for Breast Biopsy Guidance", University of North Carolina at Chapel Hill.
Tan et al., "A Versatile Learning-Based 3D Temporal Tracker: Scalable, Robust, Online", ICCV, 2015, Computer Vision Foundation.
Tong et al., "Scanning 3D Full Human Bodies Using Kinects", PubMed, Apr. 2012 DOI: 10.1109/TVCG.2012.56.
Traub et al., "Hybrid Navigation Interface for Orthopedic and Trauma Surgery", MICCAI, 2006, LNCS 4190, pp. 373-380, Springer-Verlog Berlin Heidelberg.
Trevisan et al., "Towards Markerless Augmented Medical Visualization", AMI-ARC, 2004, pp. 57-66.
Vercauteren et al., "Real Time Autonomous Video Image Registration for Endomicroscopy: Fighting thhe Compromises", SPIEBIOS, 2007.
Vogt et al., "Reality Augmentation for Medical Procedures: System Architecture, Single Camera Marker Tracking, and System Evaluation", International Journal of Computer Vision, 2006, p. 179-190, Springer Science + Business Media, LLC.
Wang et al., "Augmented Reality 3D Displays with Micro Integral Imaging", Journal of Display Technology, Oct. 2014.
Wang et al., "3D Modeling from Wide Baseline Range Scans Using Contour Coherence", IEEE, 2014.

Davies et al., "Computer Assisted Orthopaedic Surgery", 8th Annual Meeting of CAOS-International Proceedings, Jun. 4-7, 2008, Hong Kong, http://www.CAOS-International.org/.
Weiss et al., "Augmented Reality Visualization Using Image-Overlay for MR-Guided Interventions: System Description, Feasibility, and Initial Evaluation in a Spine Phantom", Musculoskeletal Imaging Technical Innovation, AJR2011; 196:W305-W307 0361-803X/11/1963-W305, Mar. 2011, American Roentgen Society.
Wilson et al., "Validation of Three-Dimensional Models of the Distal Femur Created from Surgical Navigation Point Cloud Data", CAOS, 2015.
Chen et al., "Development of a Surgical Navigation System Based on Augmented Reality Using and Optical See-Through Head-Mounted Display", Journal of Biomedical Informatics, 55, 2015, 124-131.
Yoon et al., "Technical Feasibility and Safety of an Intraoperative Head-Up Display Device During Spine Instrumentation", The International Journal of Medical Robotics and Computer Assisted Surgery, 2016.
Aguerreche L. et al., "Reconfigurable Tangible Devices for 3D Virtual Object Manipulation by Single or Multiple Users." VRST 2010, Nov. 2010, Hong Kong, Hong Kong SAR China. inria-00534095.
Azura, R., "A survey of augmented reality." Teleoperators and Virtual Environments, vol. 6, Issue 4, Aug. 1997, pp. 355-385.
Bajura, M., et al., "Merging Virtual Objects with the Real World: Seeing Ultrasound Imagery Within the Patient.", In Proceedings of SIGGRAPH '92, 1992, New York: ACM Press, pp. 203-210.
Benford, S. et al., "User embodiment in collaborative virtual environments", Proceedings of the SIGCHI conference on Human factors in computing systems, CHI '95, pp. 242-249, 1995.
Bichlmeier C., et al. "Contextual Anatomic Mimesis Hybrid In-Situ Visualization Method for Improving Multi-Sensory Depth Perception in Medical Augmented Reality.", IEEE 2007, 2007 6th IEEE and ACM International Symposium on Mixed and Augmented Reality.
Billinghurst, et al., "The MagicBook: A Transitional AR Interface.", Computers and Graphics, Nov. 2001, pp. 745-753.
Billinghurst, M., et al., "Experiments with Face to Face Collaborative AR Interfaces.", Virtual Reality Journal, vol. 4, No. 2, (2002).
Billinghurst, M., et al., "Collaborative Mixed Reality.", Communications of the ACM 2002, vol. 45 Issue 7, pp. 64-70 (2002).
Billinghurst, M., et al., "Collaborative Mixed Reality", First International Symposium on Mixed Reality (ISMR '99). Mixed Reality—Merging Real and Virtual Worlds, pp. 261-284. Berlin: Springer Verlag.
Cruz-Neira C. et al., "The cave: audio visual experience automatic virtual environment.", Commun. ACM, vol. 35, No. 6, pp. 64-72, Jun. 1992.
Fitzmaurice, G., et al., "Bricks: Laying the Foundations for Graspable User Interfaces.", Proceedings of Conference on Human Factors in Computing Systems (CHI '95), Denver, Colorado, ACM Press, 442-449, (1995).
Gee A, et al., "Processing and visualizing three-dimensional ultrasound data.", The British Journal of Radiology, vol. 77, S186-S193, (2004).
Gonzalez, Smart Multi-Level Tool for Remote Patient Monitoring Based on a Wireless Sensor Network and Mobile Augmented Reality, Sensors, Sep. 2014; 14(9): 17212-17234.
Gorbert, M. et al., "Triangles: Tangible Interface for Manipulation and Exploration of Digital Information Topography.", Proceedings of CHI '98, Apr. 18-23, 1998, © 1998 ACM.
Ishii, H., et al., "Iterative Design of Seamless Collaboration Media.", Communications of the ACM, vol. 37, No. 8, Aug. 1994, pp. 83-97.
Maier-Hein, L. et al., "Towards Mobile Augmented Reality for On-Patient Visualization of Medical Images.", Bildverarbeitung für die Medizin 2011: Algorithmen-Systeme-Anwendungen Proceedings des Workshops vom 20.—Mar. 22, 2011 in Lübeck (pp. 389-393).
Medeiros D. et al., "Proposal and evaluation of a tablet-based tool for 3D virtual environments.", SBC Journal on 3D Interactive Systems, vol. 4, No. 2, pp. 30-40, (2013).

(56) References Cited

OTHER PUBLICATIONS

Nicolau, "Augmented Reality in Laparoscopic Surgical Oncology.", Surgical Oncology, vol. 20, pp. 89-201 (2011).
Salmi Jamali, S. et al. "Utilising Mobile-Augmented Reality for Learning Human Anatomy.", 7th World Conference on Educational Sciences, (WCES-2015), Feb. 5-7, 2015, Novotel Athens Convention Center, Athens, Greece.
Schramm, Kinect: The Company Behind the Tech Explains How it Works, Jun. 19, 2010, https://www.engadget.com/2010/06/19/kinect-how-it-works-from-the-company-behind-the-tech/?guccounter=1&guce_referrer=aHR0cHM6Ly93d3cuZ29vZ2xlLmNvbS8&guce_referrer_sig=AQAAAKHcnRaFMexHHXiiRrcGjKYjWQ2VJGsMA556eCVncvte7f0VM4aN3GpWj1WqU3RfCnTwHcTbxmibv1lz_TUFgILvsRhShqXDrSM63Ocvvj1SzpUoBvsC2LsOmHqf-zifqdYe1ctf0D0MDM78YhH-u7w9JUfxuLDGVUxUi9hDQLZo.
Watsen, K., et al., "A Handheld Computer as an Interaction Device to a Virtual Environment.", Proceedings of the International Projection Technologies Workshop, Stuttgart, Germany, May 10-11, 1999.
Wellner, P., "Interacting with Paper on the DigitalDesk.", Communications of the ACM. 36, 7, 87-96, (1993).
Yamazaki, K. et al., "Gesture Laser and Gesture Laser Car-Development of an Embodied Space to Support Remote Instruction.", In Bodker, S., Kyng, M. and Schmidt, K. (eds.), Proceedings of the Sixth European Conference on Computer Supported Cooperative Work—ECSC W'99, Sep. 12-16, Copenhagen, Denmark. Kluwer Academic Publishers, Dordrecht.
Yang H. et al., "Exploring collaborative navigation.", Proceedings of the 4th international conference on Collaborative virtual environments, CVE, pp. 135-142, (2002).
Aichert et al., "Image-Based Tracking of the Teeth for Orthodontic Augmented Reality", MICCAI 2012, Part II, LNCS 7511, pp. 601-608, Springer-Verlag, Berlin Heidelberg 2012.
Andersen et al., "Virtual Annotations of the Surgical Field through an Augmented Reality Transparent Display", CrossMark, May 27, 2015, DOI 10.1007/s00371-015-1135-6.
Armstrong et al., "A Heads-Up Display for Diabetic Limb Salvage Surgery: A View Through teh Google Looking Glass", Journal of Diabetes Science and Technology, 2014, p. 951-956, vol. 8(5), Sage.
"A Look Into the Body—Augmented Reality in Computer Aided Surgery", Fakultat fur Informatik der Technischen Universitat Munchen, DOCMED.tv.
Baker et al., "The Emergence of Augmented Reality in Orthopaedic Surgery and Education", The Orthopaedic Journal at Harvard Medical School, Jun. 2015, www.orthojournalhms.org/16/article8_16.html, vol. 16.
Bauer et al., "Joint ToF Image Denoising and Registration with a CT Surface in Radiation Therapy", International Conference on Scale Space and Variational Methods in Computer Vision, 2011.
Bauer S. et al. (2013) Real-Time Range Imaging in Health Care: A Survey. In: Grzegorzek M., Theobalt C., Koch R., Kolb A. (eds) Time-of-Flight and Depth Imaging. Sensors, Algorithms, and Applications. Lecture Notes in Computer Science, vol. 8200. Springer, Berlin, Heidelberg.
Besl and McKay, "A Method for Registration of 3-D Shapes", IEEE Transactions on Pattern Analysis and Machine Intelligence, Feb. 1992, p. 239-256, vol. 14, No. 2, IEEE.
Bichlmeier et al., "Virtually Extended Surgical Drilling Device: Virtual Mirror for Navigated Spine Surgery", MICCAI, 2007, pp. 434-441, Part I, LNCS 4791, Springer-Verlag, Berlin Heidelberg.
Birkfellner et al., "Computer-enhanced Stereoscopic Vision in a Head-mounted Operating Binocular", Physics in Medicine and Biology, 2003, N49-N57, Phys. Med. Biol. 48, Institute of Physics Publishing.
Birkfellner et al., "In-vitro Assessment of a Registration Protocol for Image Guided Implant Dentistry", Clin. Oral Impl., Res 12, 2001, p. 69-78, Munksgaard.

Birkfellner et al., "A Head-Mounted Operating Binocular for Augmented Reality Visualization in Medicine-Design and Initial Evaluation", IEEE Transactions on Medical Imaging, Aug. 2002, p. 991-997, vol. 21, No. 8, IEEE.
Blackwell et al., "An Image Overlay System for Medical Data Visualization", Medical Image Analysis, 2000, 67-72, vol. 4, Elsevier Science B.V.
Blackwell et al., "Augmented Reality and Its Future in Orthopaedics", Clinical Orthopaedics and Related Research, Sep. 1998, pp. 111-122, No. 354, Lippincott Williams & Wilkins.
Blackwell et al., "An Image Overlay System for Medical Data Visualization", MICCAI, 1998, p. 232-240.
"3D Optical Microscopy for Orthopedic Implants", Bruker Nano Surfaces, AZoM.com, Jun. 17, 2016.
Daniel and Ramos, "Augmented Reality for Assistance of Total Knee Replacement", Journal of Electrical and Computer Engineering, 2016, 1-6, vol. 2016, Article ID 9358369, http://dx.doi.org/10.1155/2016/9358369, Hindawi Publishing Corporation.
Catani et al., "Knee Surgery Using Computer Assisted Surgery and Robotics", ESSKA, 2013, Library of Congress No. 2012954676, Springer Heidelberg New York Dordrecht London.
Chandak, "MEMS Based Wireless Controlled Robot with Voice and Video Camera", International Journal of Scientific & Engineering Research, Apr. 2014, p. 456-460, vol. 5, Issue 4, IJSER.
Charbonnier, "Real Virtuality: Perspectives Offered by the Combination of Virtual Reality Headsets and Motion Capture", Artanim, Aug. 23, 2015.
Cui et al., "KinectAvatar: Fully Automatic Body Capture Using a Single Kinect", 2013, Augmented Vision, DFKI.
DeLambert et al., "Electromagnetic Tracking for Registration and Navigation in Endovascular Aneurysm Repair: A Phantom Study", European Journal of Vascular and Endovascular Surgery, 2012, p. 684-689, 43, Elsevier Publishing.
Draelos, "The Kinect Up Close: Modifications for Short-Range Depth Imaging", A thesis submitted to the Gradate Faculty of North Carolina State University, 2012.
Elmi-Terander et al., "Surgical Navigation Technology Based on Augmented Reality and Integrated 3D Intraoperative Imaging", Spine, 2016, pp. E1303-E1311, vol. 41, No. 21, Wolters Kluwer Health, Inc.
Fischer et al., "Medical Augmented Reality Based on Commercial Image Guided Surgery", Eurographics Symposium on Virtual Environments, 2004, The Eurographics Association.
Flusser et al., "Image Fusion: Principles, Methods, and Applications", Tutorial EUSIPCO, 2007, Lecture Notes.
Fritz et al., "Augmented Reality Visualization with Image Overlay for MRI-Guided Intervention: Accuracy for Lumbar Spinal Procedures with a 1.5-T MRI System", Vascular and Interventional Radiology, Jun. 22, 2011, AJR2012; 198: W266-W273 0361-803X/12/1983-266, AJR:198, Mar. 2012, American Roentgen Ray Society.
Fritz et al., "Augmented Reality Visualization with Image Overlay for MR Imaging-Guided Interventions: Assessment of Performance in Cadaveric Shoulder and Hip Arthrography at 1.5T1", Radiology, Oct. 2012, p. 254-259, vol. 265:No. 1, radiology.rsna.org.
Garon et al., "Real-Time High Resolution 3D Data on the HoloLens", IEEE International Symposium on Mixed and Augmented Reality, 2016, DOI: 10.1109/ISMAR-Adjunct.2016.0073.
Garrido-Jurado et al., "Automatic Generation and Detection of Highly Reliable Fiducial Markers Under Occlusion", Pattern Recognition, Jun. 2014.
Gavaghan et al., "Augmented Reality Image Overlay Projection for Image Guided Open Liver Ablation of Metastic Liver Cancer", AE-CAI 2011, LNCS 7264, pp. 36-46, 2012, Springer-Verlag Berlin Heidelberg.
George and Kesavadas, "Low Cost Augmented Reality for Training of MRI-Guided Needle Biopsy of the Spine", Medicine Meets Virtual Reality, 2008, p. 138-140, 16, IOS Press.
Germano, "Advanced Techniques in Image-Guided Brain and Spine Surgery", 2002, Thieme Medical Publishers, Inc.
Gromov et al., "What is the Optimal Alignment of the Tibial and Femoral Components in Knee Arthroplasty", Acta Orthopaedica,

(56) References Cited

OTHER PUBLICATIONS

Sep. 2014, 85(5): 480-487, www.ncbi.nlm.nih.gov/pmc/articles/PMC4164865/, Nordic Orthopaedic Federation.

Xiaojun et al., "Development of a Surgical Navigation System Based on Augmented Reality Using an Optical See-Through Head-Mounted Display", Journal of Biomedical Informatics, 55 (2015) 124-131, Elsevier.

Hinterstoisser et al., "Multimodal Templates for Real-Time Detection of Texture-less Objects in Heavily Cluttered Scenes", 2011, ICCV.

Hinterstoisser et al., "Real-Time Learning of Accurate Patch Rectification", Proceedings/CVPR, IEEE Computer Society Conference on Computer Vision and Pattern Recognition, Jun. 20-25, 2009, Miami, Florida DOI:10.1109/CVPR.2009.5206794.

Hinterstoisser et al., "Gradient Response Maps for Real-Time Detection of Texture-less Objects", IEEE Transactions on Pattern Analysis and Machine Intelligence, 2011.

Hoff, "Fusion of Data from Head-Mounted and Fixed Sensors", Submitted to the First International Workshop on Augmented Reality, Nov. 1, 1998, San Francisco, California.

Hinterstoisser et al., "Model Based Training, Detection and Pose Estimation of Texture-less 3D Objects in Heavily Cluttered Scenes", ACCV, 2012.

"Holographic Weapon Sight", Wikipedia, https://en.wikipedia.org/wiki/Holographic_weapon_sight, Nov. 22, 2016.

Hu et al., "A Convenient Method of Video See-Through Augmented Reality based on Image-Guided Surgery System", Internet Computing for Engineering and Science, 2013, p. 100-103, IEEE, Shanghai.

Hua et al., "A 3D Integral Imaging Optical See-Through Head-Mounted Display", Optics Express, May 28, 2014, vol. 22, No. 11.

Ji and Yang, "Real-Time Eye, Gaze, and Face Pose Tracking for Monitoring Driver Vigilance", Real-Time Imaging, 2002, p. 357-377, 8, Elsevier Science Ltd.

Jolesz, "Intraoperative Imaging and Image-Guided Therapy", 2014, Springer Science + Business Media New York.

Kanade et al., "Simulation, Planning, and Execution of Computer-Assisted Surgery", 1996.

Kato et al., "Marker Tracking and HMD Calibration for a Video-Based Augmented Reality Conferencing System", Proceedings 2nd IEEE and ACM International Workshop on Augmented Reality, Oct. 20-21, 1999, DOI: 10.1109/IWAR.1999.803809.

Kim et al., "Registration Accuracy Enhancement of a Surgical Navigation System for Anterior Cruciate Ligament Reconstruction: A Phantom and Cadaveric Study", The Knee, 2017, p. 329-339, Elsevier Science.

Kolodzey et al., "Wearable Technology in the Operating Room: A Systematic Review", BMJ Innov, 2017, 3:55-63.

Kumar and Neelima, "A Portable Wireless Head Movement Controlled Human-Computer Interface for People with Disabilities", International Journal of Advance Research in Electrical, Electronics and Instrumentation Engineering, Jul. 2014, (print): 2320-3765, (online): 2278-8875, vol. 3, Issue 7.

\* cited by examiner

AUGMENTED REALITY GUIDANCE FOR SPINAL PROCEDURES USING STEREOSCOPIC OPTICAL SEE-THROUGH HEAD MOUNTED DISPLAYS WITH REAL TIME VISUALIZATION OF TRACKED INSTRUMENTS

CROSS-REFERENCE TO RELATED APPLICATIONS

This application is a continuation of U.S. application Ser. No. 16/919,639, filed Jul. 2, 2020, which is a continuation of U.S. application Ser. No. 16/822,062, filed Mar. 18, 2020, now U.S. Pat. No. 10,742,949, which is a continuation of U.S. application Ser. No. 16/598,697, filed Oct. 10, 2019, now U.S. Pat. No. 10,602,114, which is a continuation of U.S. application Ser. No. 16/518,426, filed Jul. 22, 2019, now U.S. Pat. No. 10,511,822, which is a continuation of U.S. application Ser. No. 16/240,937, filed Jan. 7, 2019, which is a continuation of U.S. application Ser. No. 15/972,649, filed May 7, 2018, now U.S. Pat. No. 10,194,131, which is a continuation of U.S. application Ser. No. 14/753,705, filed Jun. 29, 2015, now U.S. Pat. No. 10,154,239, which claims the benefit of and priority to provisional application No. 62/097,771, filed Dec. 30, 2014. The entirety of each these applications are hereby incorporated herein by reference.

BACKGROUND INFORMATION

Field of the Invention

Embodiments are directed towards image-guided surgery, and more particularly CT-guided, MR-guided, fluoroscopy-based or surface-based image-guided surgery, wherein images of a portion of a patient are taken in the preoperative or intraoperative setting and used during surgery for guidance.

Background

In the practice of surgery, an operating surgeon is generally required to look back and forth between the patient and a monitor displaying patient anatomical information for guidance in operation. In this manner, a type of mental mapping is made by the surgeon to understand the location of the target structures. However, this type of mental mapping is difficult, has a steep learning curve, and compromises the accuracy of the information used.

Equipment has been developed by many companies to provide intraoperative interactive surgery planning and display systems, mixing live video of the external surface of the patient with interactive computer generated models of internal anatomy obtained from medical diagnostic imaging data of the patient. The computer images and the live video are coordinated and displayed to a surgeon in real time during surgery, allowing the surgeon to view internal and external structures and the relationship between them simultaneously, and adjust the surgery accordingly.

Preoperative or intraoperative image registration with surface reconstruction has been done in conventional surgery navigation systems either with a single 3D scanner device that functions at the same time as video camera (e.g. time-of-flight cameras). These conventional systems display the surgeon's main viewpoint, or a video camera or stereoscopic video cameras that are used as viewpoint for the surgeon are used for processing a surface reconstruction. These conventional systems may enhance the surface reconstruction or image registration with other techniques, such as optical or infrared techniques, markers, etc. However, these systems are limited in the availability of precise 3D surfaces, in their precision and speed of image registration of preoperative or intraoperative image with the 3D surfaces, and in blending such registered images with the viewpoint of the surgeon.

Accordingly needs exist for more effective systems and methods that combine real-time preoperative images with virtual graphics associated with the preoperative images, wherein the combination of the preoperative images and virtual graphics is displayed on a stereoscopic, see through, head mounted display.

SUMMARY OF THE INVENTION

Embodiments disclosed here describe a real-time surgery navigation method and apparatus for displaying an augmented view of the patient from the preferred static or dynamic viewpoint of the surgeon. Embodiments utilize a surface image, a graphical representation the internal anatomic structure of the patient processed from preoperative or intraoperative images, and a computer registering both images. Responsive to registering the images, a head mounted display may present to a surgeon an augmented view of the patient, wherein the augmented reality is presented via a head mounted display.

Embodiments disclosed herein include a stereoscopic camera system. The stereoscopic camera system may be configured to provide real-time stereoscopic images of a target portion of the patient. In embodiments, the stereoscopic camera system may include a 3D scanner system that is configured to determine location data and orientation data, wherein the location data and orientation data are determined in reference to a common coordinate system.

Responsive to the stereoscopic camera system recording media, and determining the location data and orientation data, a stereoscopic view of the 3D volume image may be output to a stereoscopic display to the surgeon in real time. The stereoscopic view of the 3D volume image may be blended in a same position as the patient appears in the stereoscopic video images during surgery. The stereoscopic view of the 3D volume image are displayed in the preferred manner, e.g. using background subtraction techniques, the 3D volume image appearing over the patient as background model, the hands and instruments appearing as foreground objects.

Embodiments may be configured to assist in real time during surgery, wherein the stereoscopic view of the 3D volume image is presented in a surgeon's field of view in a stereoscopic manner, e.g. graphical representations of instruments tracked, surgical guides or techniques, anatomical models, etc. as needed. Accordingly, utilizing the stereoscopic view of the 3D volume image, the surgeon may be able to make adjustments to the stereoscopic view of the 3D volume image. For example, the surgeon may modify the stereoscopic view of the 3D volume image by selecting a transparency, color and contrast of each image layer displayed, using an available real-time user interface means, which may include gesture recognition methods.

Embodiments may be independent devices and processes for each main task provided during surgery: surface reconstruction and image registration, stereoscopic video and stereoscopic image registration. Embodiments may also be configured to provide an enhanced depth perception through background subtraction methods, and real-time user interaction, which may change the separation of the stereoscopic video cameras, adjusting the position of the registered 3D volume, displaying the 3D volume in a precise manner, adapting for pose change detected in the surface, adjusting the degree of transparency, color and contrast, etc.

Embodiments disclosed herein disclose systems that are configured to record stereoscopic video with at least two mounted cameras. The media record by the cameras may be in the field of view of a surgeon. Utilizing a head-mounted display, the surgeon may freely move in the operating room, keeping the desired field of vision defined by the position and orientation of the mounted cameras. With the mounted cameras and the head mounted display, the surgeon would be able to view the media recorded by the mounted cameras.

Virtual graphics may be added to the media recorded by the two cameras. Responsive to the virtual graphics being added to the recorded media, the surgeon may be presented on the head-mounted display a preoperative image, such as a 3D volume image of a previous CT. The preoperative image may be presented, recorded, or registered (referred to hereinafter collectively and individually as "registered") over the patient, in real time. Thus, the internal anatomical structures of the patient may be blended with the media recorded by the mounted cameras.

In embodiments, tracking may be configured to be added to instruments or implants within the preoperative image, wherein virtual graphics are associated with views inside the patient presented to the surgeon. Accordingly, embodiments may be configured to register preoperative images blended with virtual graphics over a target portion of a patient, wherein the blended images are presented over a visual field of a surgeon.

In embodiments, an intermediate 3D surface may be obtained by surface reconstruction via 3D scanners. The intermediate 3D surface may be used for registration with a 3D volume obtained by volume rendering via image data from a CT or MR scan. The 3D volume image of the patient may be automatically located in real time to the positioned of the patient based on a common coordinate system between the stereoscopic cameras, head mounted display, the virtual graphics, and/or the 3D surface. The 3D volume image may be any surface rendering of a preoperative image.

Tracking a 3D scanner's virtual camera and the mounted camera to the coordinate system, may define where an augmented view may be positioned on the head mounted display. Accordingly, the preoperative images may be utilized without markers, which may allow for more flexible and quicker registration.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
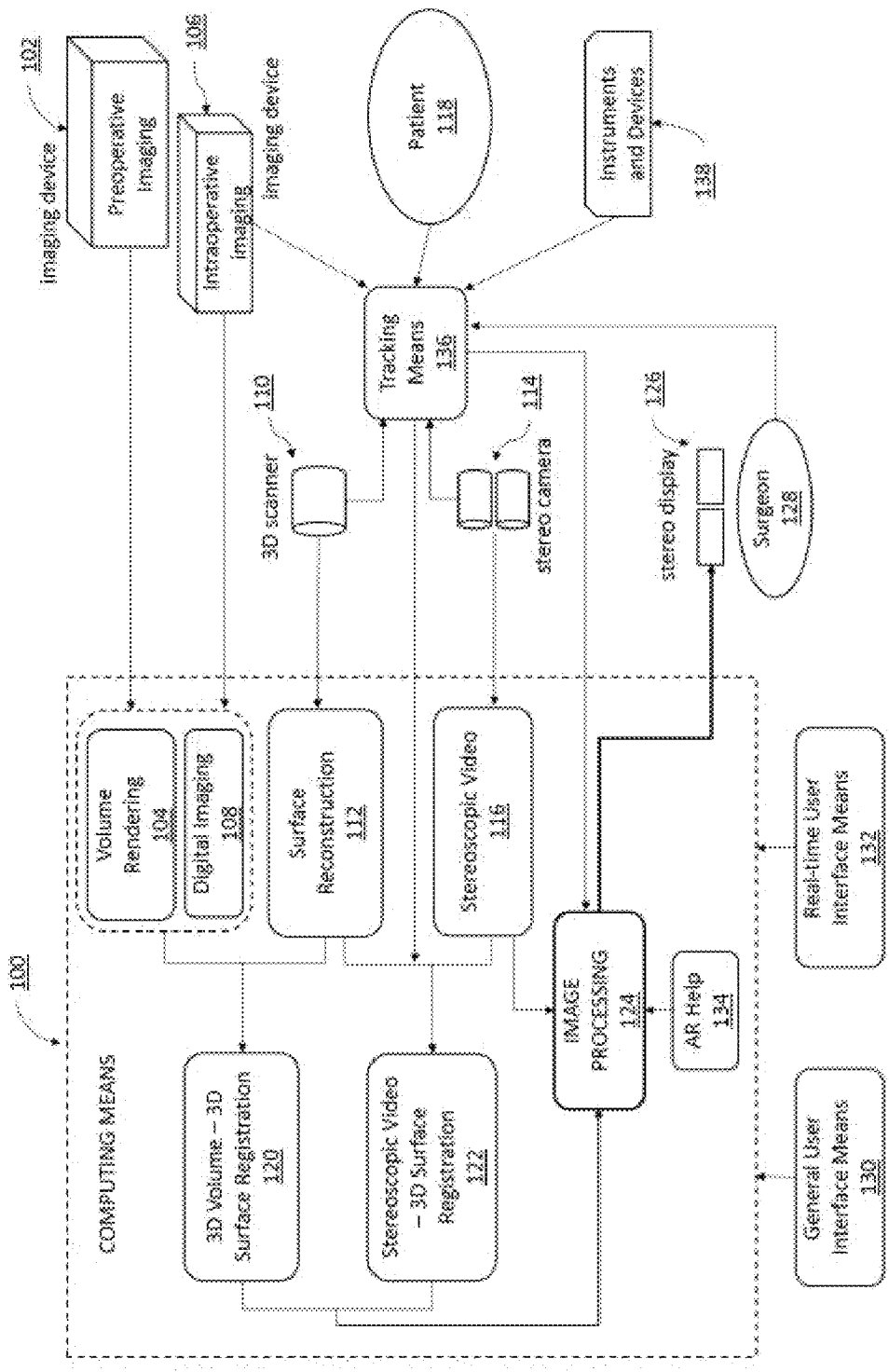
FIG. 1 shows a block diagram of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION OF THE INVENTION

In the following description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

FIG. 1 shows an exemplary embodiment of the surgical navigation system. Surgical navigation system 100 may include devices configured to create a 3D rendering of a region of interest.

Using computer means 100, volume data of a patient scanned with a preoperative imaging 102 or an intraoperative imaging 106 device (e.g. CT scanner) is rendered as a 3D volume image using a volume rendering technique 104 and stored for processing, wherein the volume data is associated with a volume of the patient. Preoperative 102 and intraoperative images 106 are also stored as digital images 108 for processing.

While computing means 110 is scanning the volume data, 3D scanner system 110 may be configured to capture a 3D surface 112 of the target portion of the patient 118, and a stereoscopic camera system (e.g. pair of cameras) 114 may be configured to obtain a stereoscopic video 116 of the scene, including the target portion of the patient 118.

Registration of the 3D volume and the 3D surface 120 is performed by computer means 100, as is the registration of the stereoscopic video with the 3D surface 122. In embodiments, registration of 3D volume 104 and stereoscopic video 116 is completed through an intermediate registration of both images with the 3D surface image 112 into a common coordinate system, The images are processed 124 and sent to the stereoscopic display 126 used by the surgeon 128. The registration and other image processing 124 by computer means 100 is adjusted by the surgeon 128 or other users through general user interface means 130 before surgery, or through real-time user interface means 132 during surgery, e.g. by interaction of the surgeon 128 with a device capable of gesture recognition (e.g. the same 3D scanner system 110 and/or stereoscopic display system 126).

User interface means 130, 132 may include graphical user interface means (e.g. virtual graphics like buttons) displayed within the surgeon's 128 view, through a 3D display 126, which may be a virtual reality, augmented reality, etc. device. Augmented reality (AR) help 134 is added to the processed images sent to the stereoscopic display system 126.

Tracking means 136, such as optical markers, may be attached to the patient 118 providing anatomic landmarks of the patient during the preoperative 102 or intraoperative images 106, and during the 3D scanning process for registration of the 3D volume with the 3D surface 120. The optical markers, alone or in combination with other tracking means, such as inertial measurement units (IMU), may be attached to the 3D scanner system 110, stereoscopic camera system 114, the surgeon 128 (e.g. in the head-mounted stereoscopic display 126), as well as to any instruments and devices 138 (e.g. screws, plates, pins, nails, arthroplasty components, etc., broaches, screwdrivers, motors, etc.) used by the surgeon 128. Utilizing tracking means, systems may offer real-time data for a more precise location and orientation of images and objects in the common coordinate system used. The stereoscopic video 116 may be sent directly to the stereoscopic display 126, without undergoing image processing 124, if the surgeon 128 or other users select that option using the available interface means 130, 132.

Figure 2:
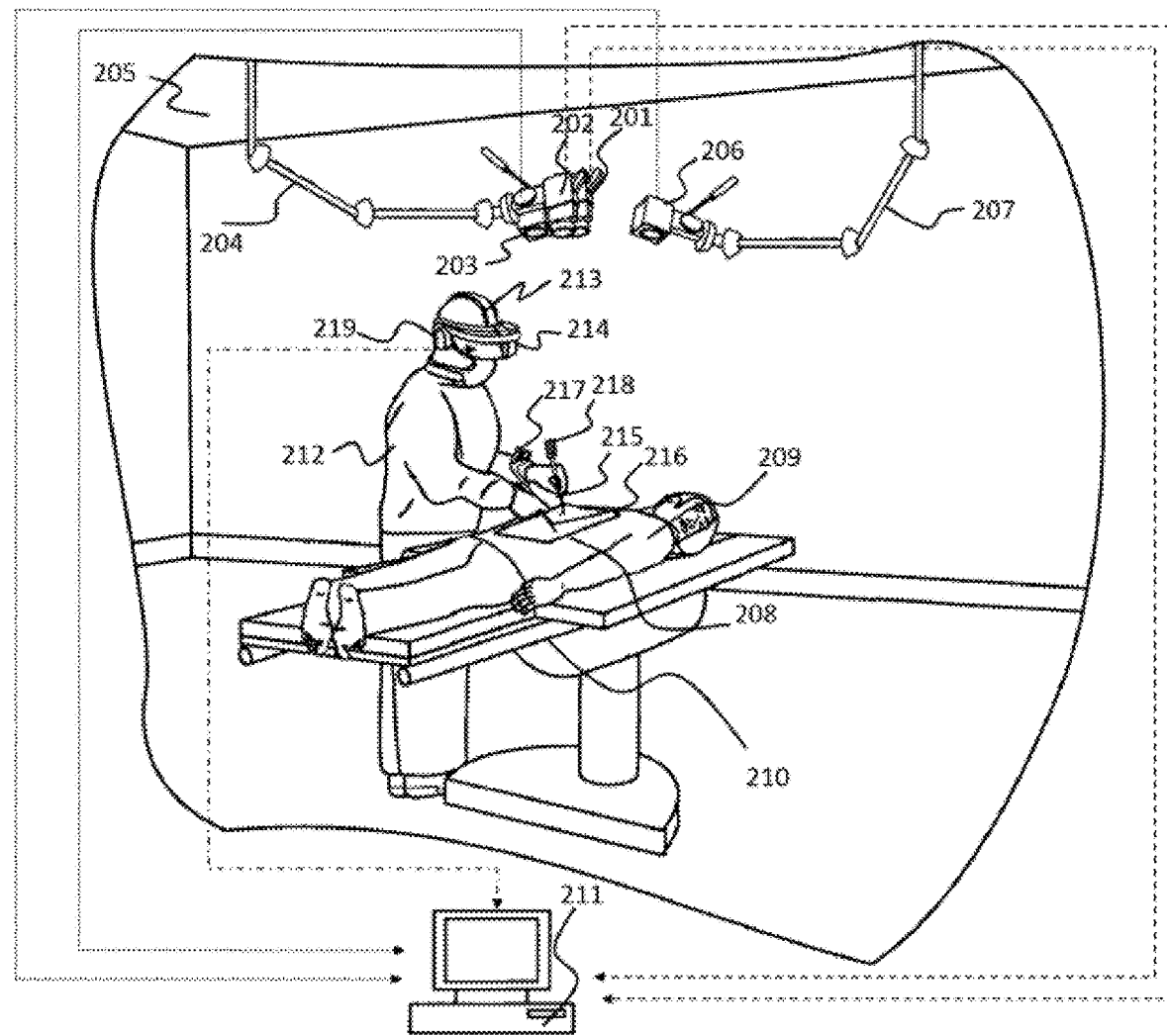
FIG. 2 shows a perspective view of a surgery navigation system of the present invention.

FIG. 2 shows an embodiment of an example of the perspective view of this navigation system in a model operating room. As depicted in FIG. 2, a pair of video cameras 201, 202 (corresponding to the stereoscopic camera system 114 in FIG. 1) may be configured to capture a stereoscopic view 116 of a region of interest. In FIG. 2, a 3D scanner 203 (corresponding to the 3D scanner system 110 in FIG. 1) is positioned proximate to the stereoscopic cameras 201, 202, in a known location and orientation angle with respect to them. The cameras 201, 202 and 3D scanner 203 are attached e.g. to an articulated mechanical arm 204 that is suspended from the ceiling 205. A second 3D scanner 206 (also part of the 3D scanner system 110), e.g. with motion tracking capabilities, is attached to another mechanical articulated arm 207.

The 3D scanners 203, 206 capture a 3D surface 112 of the target portion 208 of the patient 209 located on a surgical table 210. Images and data obtained from 3D scanners 203, 206 is stored and processed in the computer 211 (corresponding to the computer means in 100 in FIG. 1) used for image processing, and the surgeon 212 and other users are able to interact with it through the available interface means 130, 132 (e.g. gesture recognition, or mouse and keyboard). The processed images 124 (e.g. stereoscopic video 116 blended with stereoscopic 3D volumetric images 104 of the internal anatomical structures) are displayed to the surgeon 212 wearing the head-mounted 213 stereoscopic display 214 (corresponding to the stereoscopic display system 126 in FIG. 1) in real time. Instruments 215, 216 are tracked e.g. by markerless optical means (e.g. using the 3D scanners 203, 206 in real time), by optical means using markers 217, by inertial measurement units 218, or a combination of these and other tracking means.

To the surgeon 212, the internal structures of the patient 209 appear directly superimposed on the target portion of the patient 208 with the selected transparency, or the selected layers of the stereoscopic 3D volumetric images appear blended with the stereoscopic video 116, or only the 3D volumetric images 104 are shown, or any other stereoscopic images from the sources available are shown to the surgeon 212, modified by any software-implemented change, like zoom, color or contrast adjustments, depending on the previous 130 or real-time interaction 132 to modify the image processing 124.

Responsive to surgeon 212 moving his or her head around to view the spatial relationship of the structures from varying positions, computer means 100 may be configured to provide the precise, objective registration between the digital images of the internal structures 104, 108 and the surface reconstruction 112 of the portion of the patient 208. This in situ or "augmented reality" visualization gives the surgeon 212 intuitively based, direct, and precise access to the image information in regard to the surgical task. Headphones 219 include sound to the augmented reality experience of the surgeon 212, who can hear the different steps of the surgery as it develops, or the advice of other professionals in a different place, who may be seeing the same images displayed to the surgeon 212, thanks to online communication.

Figure 3:
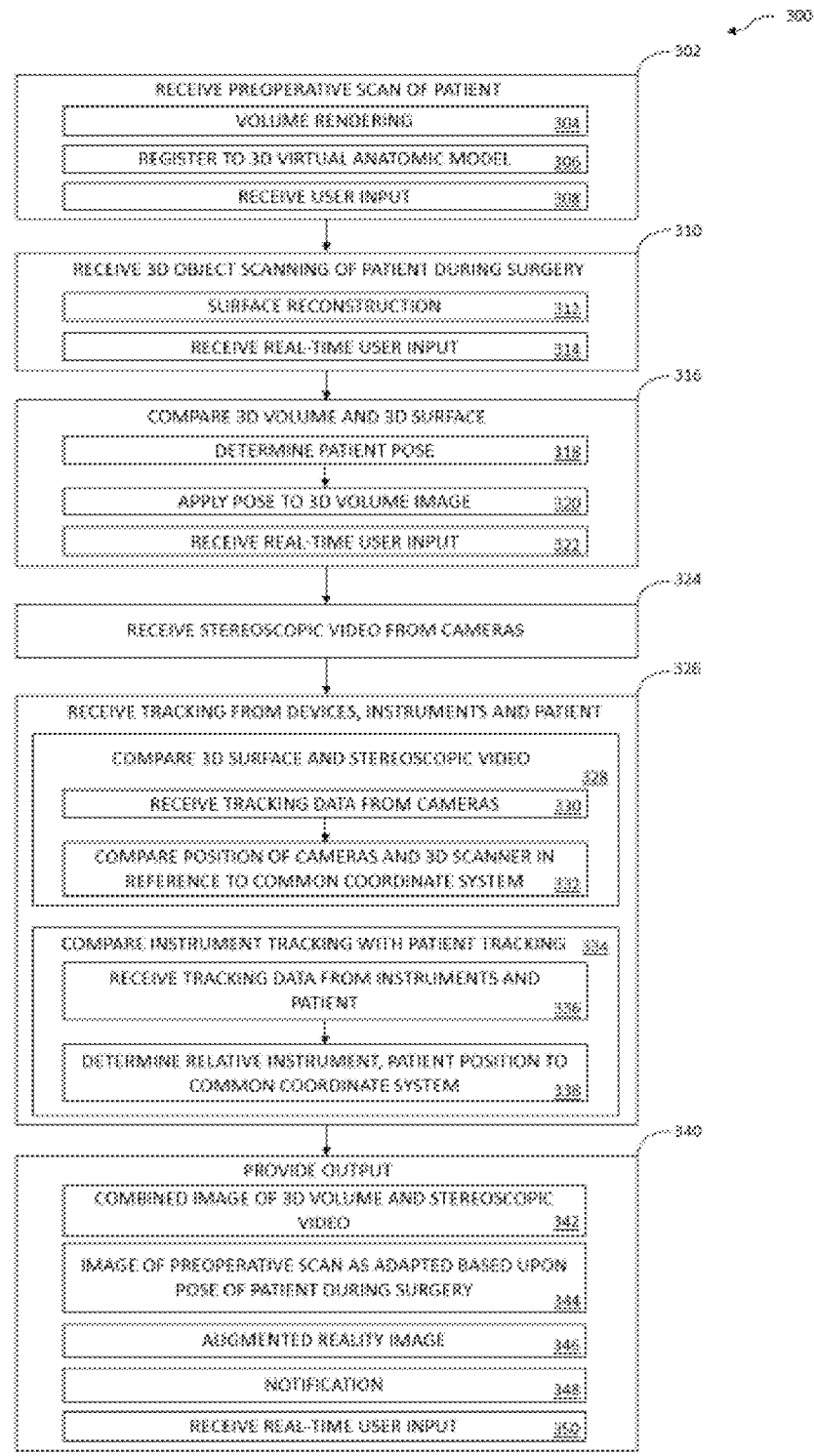
FIG. 3 shows a flow diagram of a method of the present invention.

FIG. 3 shows a flow diagram depicting an embodiment of a method 300 for integrating preoperative 102 and stereoscopic video 116 images. The operations of method 300 presented below are intended to be illustrative. In embodiments, method 300 may be accomplished with one or more additional operations not described, and/or without one or more of the operations discussed. Additionally, the order in which the operations of method 300 are illustrated in FIG. 3 and described below is not intended to be limiting.

At operation 302, the computer 100 receives preoperative image data (e.g. CT scan) 102.

At operation 304, the preoperative image data is processed into a 3D volume by a volume rendering technique (which is the same as the volume rendering 104 in FIG. 1). The volume rendering technique may be based e.g. on segmentation of the volume data of the anatomic internal parts of the portion of the patient 118.

At operation 306, one or more graphical representations of the imaged structures may be provided. Operation 306 may be performed with user interaction at Operation 308 (before or during surgery), using the available user interface means 130, 132.

At operation 310, a 3D scan of the patient may be received.

At operation 312, a precise surface reconstruction of the patient (which is the same as the surface reconstruction 112 in FIG. 1) may be constructed automatically.

At operation 314, the surface reconstruction of the patient may be adjusted with input from the surgeon 128 or other users.

At operation 316, the 3D volume rendering and the surface reconstruction may be compared by automated means.

At operation 318, the pose of the patient may be determined during surgery.

At operation 320, the 3D volume may be adjusted according to the determined pose. More specifically, the 3D volume may be adjusted so that the orientation of the 3D volume as displayed to the surgeon matches the orientation of the portion of the patient on which the surgeon is operating.

At operation 322, the surgeon or other users may be able to correct, in real time, the pose.

At operation 324, the computer may receive stereoscopic video (which is the same as the stereoscopic video 116 in FIG. 1) from the stereoscopic camera system.

At operation 326, tracking means attached to the 3D scanner system 110, stereoscopic camera system 114, patient 118, imaging devices 106, and instruments 138, may send data to the computer 100. The computer may process and store the received data 326. For example, the received data may include 3D surface and stereoscopic video.

At operation 328, the 3D surface data and data associated with the stereoscopic video may be compared.

At operation 330, orientation tracking data of each of the cameras that form the stereoscopic camera system may be obtained. The obtained orientation tracking data may be used in combination with the appropriate tracking means 136 for location.

At operation 332, a view of the 3D surface may be displayed to the surgeon, wherein the view corresponds to the precise position of each camera in the common coordinate system.

At operation 334, patient tracking data may be compared with instrument or device tracking data, e.g. with data from inertial measurement units and optical markers placed on the patient 118, and/or instruments 138.

At operation 336, the patient tracking data may be received by the computer.

At operation 338, the patient tracking data may be automatically processed, which may be configured to locate all tracked objects within the common coordinate system. Utilizing the common coordinate system and the patient tracking data, a visualization associated with the patient tracking data within the common coordinate system may be displayed to the surgeon or other users in real time, e.g. in numeric or graphic format. Accordingly, the position of the cameras forming the stereoscopic camera system 114 may be dynamically determined, and utilizing the position of the cameras the precise location and orientation of the 3D surface model with respect to the view of each camera 114 may be determined. The position of the data recorded by each camera 114 in the common coordinate system corresponding to the position of the virtual cameras may offer a view of the 3D surface.

At operation 340, a blended image output may be presented on the stereoscopic display 126. At operation 342, registration of the 3D volume and the stereoscopic video is done with help from an intermediate 3D surface reconstruction. This process may be fully automatic by software means, or may be performed with help from user interaction.

At operation 344, the registration of the 3D volume and the stereoscopic video may account for pose changes of the patient, and it is displayed to the surgeon according to the precise location of the cameras 114, so that there is a seamless integration of all views (e.g. video, 3D surface and 3D volume) to both eyes.

At operation 346, the images are displayed stereoscopically to the surgeon 128 in real time. The images may depict an augmented reality image or "augmented view."

At operation 348, the augmented reality image may include notification helps 348.

At operation 350, the surgeon 128 or other users may perform actions to input data into to the system in real time during surgery using the available user interface means 132. Thus, modifying the image processing 124 and customizing the view shown in the display 126.

Returning to FIG. 2, the stereoscopic camera system 114 captures a stereoscopic view of the scene, wherein the stereoscopic camera system 114 is comprised of a pair of cameras 201, 202. The cameras 201, 202 may be positioned at a certain distance from each other. This distance is adjusted depending on the interpupillary distance of the surgeon 212, and on the distance from the cameras 201, 202 to the target field of view, usually centered on the target portion of the patient 118. The computer 211 receives the video images 116 and sends them to the stereoscopic display 219, with or without modifications through image processing 124, such as additional virtual graphics, zoom, color or contrast adjustments.

In embodiments, as depicted in FIG. 2, the pair of cameras 201, 202 may be attached to an articulated mechanical arm 204 that is e.g. suspended from the ceiling 205. In this exemplary embodiment, the 3D scanner 203 is in a fixed position close to the cameras 201, 202, so that location and orientation tracking between the devices is not necessary. Alternatively, the 3D scanner 206 may not be in a fixed position with respect to the cameras 201, 202, and is e.g. attached to another articulated mechanical arm 206 suspended from the ceiling 207.

Figure 4:
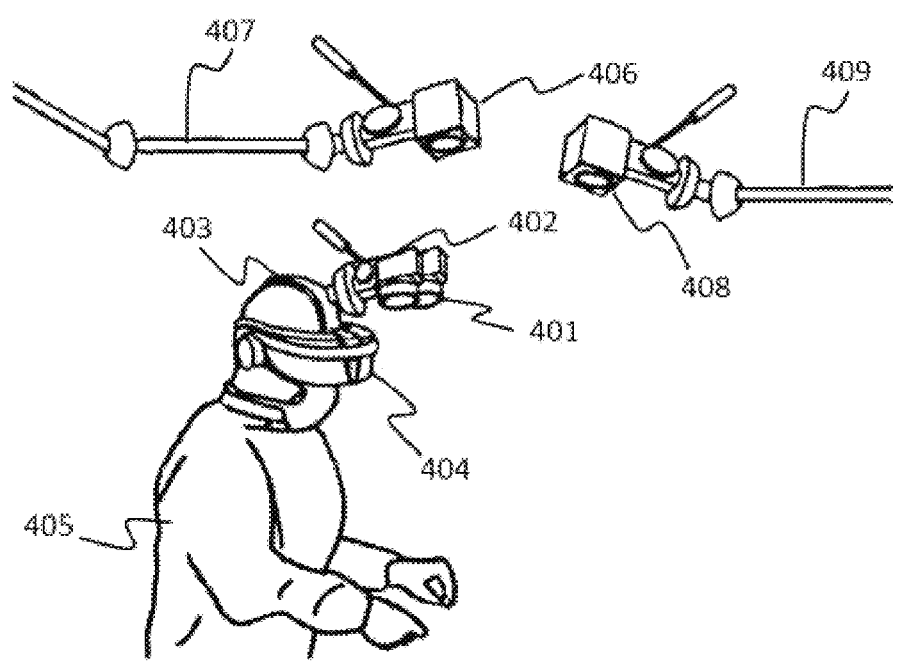
FIG. 4 shows a perspective view of the surgery navigation system of the present invention.

Turning now to FIG. 4, the cameras 401, 402 are head-mounted 403 along with the stereo display 404, and worn by the surgeon 405. The 3D scanner 406 is attached to an articulated arm 407, or alternatively, a 3D scanner is also head-mounted close to the cameras 401, 402. An additional 3D scanner 408 (e.g. with motion tracking capabilities, as a time-of-flight camera) is e.g. attached to an articulated mechanical arm 409 e.g. suspended from the ceiling, or placed on the ground, or in any other suitable location.

Figure 5:
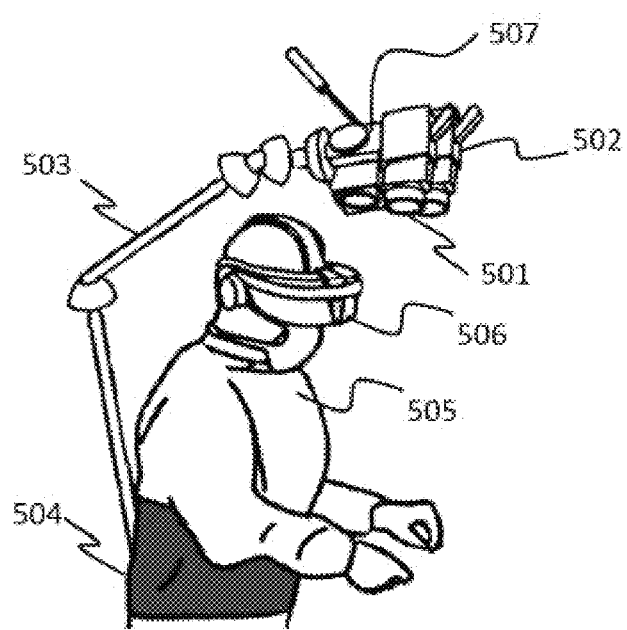
FIG. 5 shows a perspective view of the surgery navigation system of the present invention.

Turning now to FIG. 5, the cameras 501, 502 are mounted on a pole 503 attached to a belt 504 worn by the surgeon 505, who sees the scene through the head-mounted stereo display 506. The 3D scanner 507 is attached to the same pole 503. Alternatively, or in combination with the other embodiments, a 3D scanner is attached to an articulated mechanical arm e.g. suspended from the ceiling, or placed on the ground. Alternatively, a 3D scanner is mounted on tripods standing on the ground. Alternatively, the camera system 114 is composed of a single, two-dimensional camera, used in combination with a camera from the 3D scanner system 110. It will be understood that the above-described examples of the number and alternative positions of cameras composing the stereoscopic camera system 114 (as well as the number and position of devices composing the 3D scanner system 110) are presented for the purpose of example, and are not intended to be limiting in any manner.

In embodiments, the surgeon 212 is able to move and rotate the cameras 201, 202 during surgery. This is done for example through interaction with the computer system 211 that controls the mechanical arm 204 movement, e.g. with gesture recognition by the stereoscopic display 214 (e.g. virtual reality display), or by the 3D scanner 203 (e.g. time-of-flight camera with motion tracking), or with voice commands by voice recognition from an appropriate device. A third person can also interact directly with the computer 211, e.g. according to the surgeon's 212 commands.

In embodiments the stereoscopic camera system 114 is mobile, fitting the evolving needs of the surgery through changes in location and orientation. Or alternatively the cameras 114 are placed fixed in a certain part of the operating room as previously designed, to fit the potential needs of the surgeon 128.

In embodiments, the cameras composing the stereoscopic camera system 114 may have special lenses (e.g. fisheye lenses, or wide-angle lenses) and they are arranged e.g. vertically side by side, to obtain a wider view and allow for the use of a virtual reality display, from those commercially available, according to each virtual reality device's preferred camera configuration. The movement of the surgeon's 128 head is tracked by the device, and the field of view of the surgeon 128 can change, while the cameras remain fixed.

In embodiments, the stereoscopic camera system 114 is composed of three or more cameras, used to obtain different stereoscopic views, e.g. arranged in circle for a combined 360° view (for example in combination with a virtual reality display), or e.g. arranged following the outline of the target portion of the patient 118. The stereoscopic video 116 of the scene displayed to the surgeon 128 changes by selecting a different camera pair through computer means 100, without the need to move the cameras, for example automatically when the surgeon 128 traverses a certain location, or by interaction of the surgeon 128 or a third person through the real-time user interface means 132.

The stereoscopic camera system 114 may be configured to provide the same images for all operating surgeons, or alternatively each surgeon may have a different stereoscopic video image displayed to him or her, or alternatively some surgeons share a view and others have individual views, depending on the needs of the surgery and the preferences of the individual surgeons.

Returning now to FIG. 1, the preoperative 102 or intraoperative image 106 information, may be received from a CT scan or an MR scan, as well as ultrasound, PET, and C-arm cone-beam computed tomography. Preoperative X-ray and stereoscopic X-ray images, intraoperative fluoroscopic and stereoscopic fluoroscopic images, and other image modalities that allow for stereoscopic and 3D representations are also used, either directly in a digital format 108, or as graphical 3D volumetric representations 104 of the image data.

The volume rendering may be a set of techniques used to display a two-dimensional (2D) projection of a 3D discretely sampled data set, typically a 3D scalar field. Computer means 100 may be configured to process the 3D data set (e.g. a group of 2D slice images acquired by a CT or MRI scan) with a volume rendering 104 technique, and provide one or more graphical representations of the imaged structures, which may include the 3D volume image representing the anatomic internal parts of a portion of the patient 118.

The volume rendering 104 techniques include 3D surface rendering, 3D volume rendering, as well as fusion, parametric mapping, and multi-object rendering. More precisely, the volume rendering 104 may be done using one or more of the available methods, such as direct volume rendering (e.g. volume ray casting, splatting, shear warp, texture-based volume rendering, etc.), maximum intensity projection, hardware-accelerated volume rendering, and any of the available optimization techniques (e.g. empty space skipping, early ray termination, volume segmentation, image-based meshing, pre-integrated volume rendering, etc.). Such methods may be further helped by the user by using regions (ROI) or volumes of interest (VOI), lookup tables (LUT), and any of the available methods for refining the volume rendering 104. It will be understood that these examples of volume rendering methods and their outputs are presented for the purpose of example, and are not intended to be limiting in any manner.

For example, 2D slice images are acquired by a CT scan, a virtual camera is defined in space relative to the volume, iso-surfaces are extracted from the volume and rendered e.g. as polygonal meshes, or directly as a block of data. In this context, a graphical representation may be a data set that is in a "graphical" format (e.g. stereolithography or STL format), ready to be efficiently visualized and rendered into an image. The surgeon 128 or other users can selectively enhance structures, color or annotate them, pick out relevant ones, include graphical objects as guides for the surgical procedure and so forth. This pre-processing may be completed offline, in preparation of the actual real-time image guidance, through the available general user interface means 130, or it may be done (or the previous preparation adjusted) during surgery, using the available real-time user interface means 132. In embodiments, virtual cameras that provide the 3D volume image may be positioned in space relative to the volume data, wherein the virtual cameras are correspondingly positioned to the common coordinate system, e.g. in the same position as the cameras composing the stereoscopic camera system 114, and/or in the same position as the devices composing the 3D scanner system 110, to allow for an easier and quicker registration of images, according to the different embodiments described.

In embodiments, two-dimensional images (e.g. fluoroscopic intraoperative images, X-rays, ultrasonographic images, etc.) are also used as 3D volume images of the target portion of the patient 118, using any of the available methods, e.g. 2D-3D reconstruction using statistical shape models, as e.g. a distal femur 3D reconstruction from registration of an X-ray imaging (e.g. lateral and anteroposterior projections) of the femur, with a 3D statistical shape model of the distal femur, with adjustments made by the surgeon 128 or other user, through the available user interface means 130, 132.

In embodiments, that 2D-3D registration of intraoperative or preoperative 2D images is done with help from volume rendering 104 of the available images (e.g. from CT scan or MR scan of the target portion of the patient 118) or from the surface reconstruction 112 of anatomical structures of the patient done during surgery. For example, in a pelvis fracture involving a hemipelvis, registration of the 2D or stereoscopic fluoroscopic intraoperative images 106 of the affected hemipelvis is done e.g. with a statistical shape model of a hemipelvis, or with the 3D volume of the CT scan of the healthy contralateral hemipelvis, or a combination of them, with interaction of the surgeon 128 and other users in real time, to obtain a precise 3D graphical representation of the fracture reduction obtained during surgery, before proceeding with the definitive fixation. In embodiments, a 3D scanner system 110 may be composed of one or more devices capable of capturing shapes of objects (and sometimes its appearance, e.g. color), usually outputting a point cloud as a data file, allowing for the construction of three-dimensional surface models of the object scanned. For example, a 3D scanner system 110 may include a laser scanner, a time-of-flight 3D laser scanner, a structured-light 3D scanner, hand-held laser scanner, a time-of-flight camera, a depth camera, or a combination of these or other devices.

The 3D scanner 110 may be moved around the target portion of the patient 118 to obtain a precise 3D surface image of it through surface reconstruction 112. For example, computer means 100 may receive a dense 3D point cloud provided by the 3D scanning process, that represents the surface of the target portion of the patient 118 by a point cloud construction algorithm, e.g. by the intersection of two lines emanating from the camera center, or from the midpoint of a line perpendicular to these two lines. After the data acquisition, some type of smoothing of the data (e.g. Gaussian) may suppress random noise.

In embodiments, the point cloud obtained is used directly for registration purposes, e.g. by comparing it with point clouds used to represent volumetric data from preoperative 104 or intraoperative imaging 106. In embodiments, computer means 100 make use of techniques of surface reconstruction 112 (e.g. Delaunay triangulation, alpha shapes, ball pivoting, etc.) for converting the point cloud to a 3D surface model (e.g. polygon mesh models, surface models, or solid computer-aided design models). The surface reconstruction 112 is fully automated by computer means 100, and can be assisted 314 by the surgeon 128 or other users through the available user interface means 130, 132.

The 3D scanning and surface reconstruction 112 of the target portion of the patient 118 is made when the surgeon 128 desires the 3D scanning and surface reconstruction, through interaction with software means 132. Alternatively, 3D scans are made after a predetermined amount of time has passed since the last scan. Alternatively, 3D scans are made whenever computer means 100 detect movement of the portion of the patient 118 (i.e. determining patient pose 318), e.g. by comparing a surface reconstruction obtained from the stereoscopic video 116 to the last surface reconstruction 112 of the 3D scanner 110, or by marker-based optical tracking, or by IMU tracking, or any other tracking means 136.

In embodiments, multiple 3D scanners are used to make a reconstruction of the surface 112 of the target portion of the patient 118 without a need for movement of the devices composing the 3D scanner system 110, or limiting the movement needed for each device. In another embodiment, multiple 3D scanners are also used for optical tracking 136 of instruments and devices 138, and for determining their location and orientation. In another embodiment, a handheld 3D scanner is used, e.g. a portable 3D scanner forming part of the 3D scanner system 110 is held in the hand and moved around the target portion of the patient, and once the desired surface is obtained, it is placed in a previously defined fixed position.

In embodiments, the 3D scanner system 110 is composed of a dedicated stereoscopic camera system, composed of at least a pair of 2D video cameras. The stereoscopic camera system may be configured to capture stereoscopic video images, wherein the cameras are positioned in a desired position with respect to the other cameras forming the system to obtain the more precise surface reconstruction. The two-dimensional images taken by the cameras are converted to point clouds or mesh surfaces, or both, using known methods for surface reconstruction, for example range imaging methods (e.g. structure-from-motion). Such surface reconstruction from images of two-dimensional cameras may be used alone, or in combination with a more precise 3D scanner to make the surface model 112 obtained (and its location and orientation angle with respect to the stereoscopic camera system 114), more accurate.

In embodiments, the 3D scanner system 110 is composed of time-of-flight cameras and/or other motion tracking devices, which are used for gesture recognition by software means, allowing for interaction of the surgeon 128 or other users with the computer 100 during surgery through the real-time user interface means 132, without touching anything in the operating room. Alternatively or in addition to gesture recognition, voice commands are used to avoid touching the computer 100 or other devices included in this invention and controlled by computer means 100.

In embodiments, the 3D scanner system 110 is composed of devices capable of real-time scanning (e.g. time-of-flight cameras), which are used to obtain an instant, real-time registration of the 3D surface 112 with the 3D volume 120 and the stereoscopic video 122 throughout the surgery. Blending that real-time 3D surface 112 with one acquired with a more precise device (e.g. 3D laser scanner), a more adaptable, real-time registered surface reconstruction is obtained, offering an instant, high-quality image registration during surgery.

In embodiments, the actual shape of the patient's body may be configured to be rendered into a 3D volume, such that fitting the overall shape of the 3D surface model to the patient 118 results in fitting of the model internal anatomy to the patient 118.

The 3D/3D registration, such as the 3D volume—3D surface registration 120, as well as 2D/3D registration, is done by computer means 100. In embodiments, rigid registration methods are used, such as geometry-based, paired-point, surface-based, intensity-based, etc. In embodiments, nonrigid registration methods are used, e.g. feature-based, intensity-based, etc. In embodiments, biomechanical models, such as statistical shape models, are incorporated into the registration method. In embodiments, registration is done with the help of optical markers, e.g. color or reflective markers in certain predefined anatomical landmarks of the patient 118 for the 3D scanner system 110, corresponding to markers of the same size and shape placed on the same predefined anatomical landmarks of the patient 118 during the preoperative 102 or intraoperative imaging 106 (e.g. radiopaque markers for CT or x-ray imaging), or virtual markers placed on the predefined anatomical parts in the graphical representation of the images obtained, in the preoperative or intraoperative setting, through the available user interface means 130, 132. In other embodiments, a combination of rigid and nonrigid registration methods are used.

For example, a markerless registration method may be used. More specifically, an output of the surface reconstruction 112 is stored in point sets or depth maps. The markerkless registration may be completed by applying known methods (e.g. the iterative closest point algorithm, the Curie point depth algorithm, or the scale invariant feature transform algorithm) to the output of volume rendering 104 (e.g. 3D volume image). This markerless registration may be completed by 2D or stereoscopic digital images 108 from previous imaging studies 102 or intraoperative images 106 (e.g. CT scans or MR scans).

Point matching is done either directly or with previous transformations to obtain more accurate outputs, e.g. calculating Gaussian curvature from the depth map, or excluding outliers (e.g. with random-sample consensus) during point matching. With the matching results, aligning the two coordinate systems is computed with software (e.g. Procrustes analysis). For a more precise registration, the preoperative images 102 are adjusted to the software needs (e.g. through segmentation by a histogram-based threshold). It will be understood that these registration methods are presented for the purpose of example, and are not intended to be limiting of the actual 3D volume—3D surface registration 120 method used in any manner.

In embodiments, registration 120 is done in a fully automated manner by computer means 100. In embodiments, the surgeon 128 or other users may adjust 322 the 3D volume—3D surface registration 120 in real time during surgery through the available user interface means 132, as described below in the different embodiments. In embodiments, the 3D volume—3D surface registration 120 is made before surgery matching the volume rendering 104 to a preoperatively done surface reconstruction 112 of the target portion of the patient 118 (e.g. in the most likely position that the patient 118 will have during surgery), and then a real-time 3D surface—3D surface registration is done during surgery.

Embodiments may be configured for real-time correction of patient pose in the 3D volume rendering 320. For example, the 3D scanner system 110 obtains the surface reconstruction 112 of a target portion of the patient 118, the surface being e.g. the superficial skin of the patient 118, and the 3D surface is blended by computer means 100 with the 3D volume of the preoperative imaging 102 (e.g. CT scan) of the patient 118. The blended part being e.g. the 3D volume of the skin surface, preferably by using preselected constant anatomic landmarks, e.g. the prominent spinous processes in the skin surface of the patient's 118 spine.

The internal anatomic structures are therefore displayed based on the positioning of patient 118 was when the preoperative image 102 was obtained, e.g. with the patient 118 in the supine position during the CT or MR scan. Responsive to performing a medical procedure on the target anatomic structures, and e.g. bony structures or soft tissues are (partially) exposed, a new 3D scan is obtained with the 3D scanner system 110. The new 3D surface obtained of the visible bones and soft tissues is blended with the 3D volume of bone and soft tissue structures, which may result in a more accurate registration of both images 120. This may be due to skin and subcutaneous fat tissue of the patient 118 changing more than internal anatomic structures during the time passed between the preoperative imaging 102 and the actual surgery.

The 3D surface is therefore used to determine the pose of the portion of the patient 118 during surgery 318, and adjust the presentation of the 3D volume, which is based upon a pose 320, so that the location and orientation of the 3D volume as displayed to the surgeon 128 matches the location and orientation of the body part of the patient 118 on which the surgeon 128 is operating. That adjustment of the pose change correction 320 is done by automatically processing new surface reconstructions 112 in real time. Alternatively, creating pose change corrections 320 is done in fixed intervals; alternatively, it may be done at the surgeon's 128 discretion Alternatively, creating pose change corrections 320 is done whenever deeper dissection has been carried out, or when the patient 118 has moved, as detected e.g. by tracking means 136. The surgeon 128 or other users are able to correct the pose change adjustments 320 made in real time 322 through the available user interface means 132.

In embodiments, markers are attached to the selected anatomic landmarks of the patient 118, to define and locate its position in the common coordinate system. Thus computer means 100 can calculate changes in position, and when a predetermined minimum (angle or distance) threshold is crossed, it rescans the portion of the patient 118 and constructs a new 3D surface 112.

In embodiments, pose changes detected 318 in the surface reconstruction 112 are translated into the 3D volume image. The detected pose changes may be translated by adjusting the supposed movement of the internal anatomic mobile parts. The supposed movement of the internal anatomic mobile parts may be detected from external pose changes when anatomic parts are individualized in the 3D volume image, which may be done preoperatively, e.g. during or after the volume rendering 104 of preoperative images 102, using the available user interface means 130. The movement of the body is tracked and translated into the movement of internal anatomic parts of a virtual anatomical (e.g. skeletal) model 306, with the help of computer means 100. In that manner, instead of blending a 3D surface with a static 3D volume image directly, the pose change 318 in the 3D surface is interpreted by computer means 100 and applied 320 to a predefined virtual anatomical model 306, to which the 3D volume of the patient is registered, obtaining more precise positions of the internal anatomic parts, e.g. location and orientation of joints and bones by using an anatomic skeletal model.

For example, if the target portion of the patient 208 is the spine, the volume rendering 104 of a previous CT scan may obtain individually rendered parts. A virtual 3D anatomic skeletal model 306 of a spine is previously developed, being mobile, and translating variations in trunk position into e.g. movement of the different vertebrae. By registration of the individualized vertebrae of the 3D volume images and the vertebrae of the virtual 3D anatomical model 306, a virtual anatomic avatar of the patient's spine is developed. Pose changes in surface reconstructions 112 are recognized by software means 318, and are automatically translated into movement of the individualized parts in the 3D anatomical avatar 320. Thus, usually supine position of the patient 118 during CT scan image is automatically turned into the most common prone position of the patient 118 in the operating room. This may be performed by translating changes to the sagittal position of the reconstructed 3D surface 112 of the spine to the position of each individual vertebra and intervertebral disk in the anatomical model, which may be the 3D volume of each vertebra and intervertebral disk.

In that manner, the system may also be configured to determine changes in lateralization and rotation of the trunk in the 3D surface into the position of individual vertebrae, vessels and nerves in the 3D volumetric image. In this manner, bone structures are more precisely located when dissecting through soft tissue (to achieve the best possible exposure), or when targeting bony structures, as in positioning of transpedicular screws. For example, when dissection is carried out to the level of bone, and individual vertebrae are seen, a new surface reconstruction 112 more accurately delimits the position and rotation of processes, laminae, pedicles and posterior body of the vertebrae. Hence, the blending of 3D surface 112 with virtual 3D anatomical model, and registration with 3D volume 120. Using appropriate segmentation and software that takes into account such variations, provides a more precise location and orientation of each individual bony and soft tissue structure, including adjacent vascular and neurological structures at risk.

As another example, in percutaneous surgery for fractures, an individualized volume rendering 104 is done of each fracture fragment in the injured portion of the patient 118, as well as of the corresponding healthy part, usually the contralateral limb or hemipelvis. The computer 100 may be configured to determine pose changes in the different surface reconstructions 112 of external and internal structures in the injured part. The computer may be configured to translate these movements to the 3D rendered fracture fragments in the virtual anatomical model of the injured part, changing their position in the virtual representation to accurately reproduce their real-time location and orientation. Reduction of fragments is then adjusted with the help of the target virtual anatomical model of the healthy part (e.g. a skeletal virtual model), which is output superimposed with the desired level of transparency to the injured part.

Intraoperative images 106 in combination with computer vision methods and real-time user interface means 132 help the surgeon 128 position the 3D volume image of individual fragments where they are in real time, as seen on the stereoscopic video 116.

When developing the virtual anatomical avatar for any location of the body, known detailed muscles, ligaments, etc., bone models are used to translate movements as precisely as possible. Such complex dynamic anatomical models are received and stored in the computer 100 from available dynamic simulation models, or they may be newly created based on the specialized literature. To apply these simulation models to a detailed 3D anatomical model, available models are stored and used, or a newly created 3D anatomy model may be created for that purpose.

In the exemplary embodiment described above in FIG. 2, the stereoscopic cameras 201, 202 and the 3D scanner 203 are closely arranged in a precise fixed and known relative position to each other, so that the precise relative location $(x_1,y_1,z_1)$ and orientation angle $(\alpha_1,\varphi_1,\theta_1)$ of the first camera 201 with respect to the 3D scanner 203, and the relative location $(x_2,y_2,z_2)$ and orientation angle $(\alpha_2, \varphi_2,\theta_2)$ of the second camera 202 with respect to the 3D scanner 203 are known. The relative locations may be used by the computer 211 to automatically select the position of virtual cameras for stereoscopic views of the 3D surface, according to the precise position of the cameras 201, 202 relative to the coordinate system used by the 3D scanner 203. The virtual cameras that define the views of the 3D surface reconstruction 112 change their location and orientation angle simultaneously as the devices composing the stereoscopic camera system 114, automatically by computer means 100, with help from data acquired from tracking means 136 on the cameras.

In embodiments, the position of the 3D scanner system 110 may be the reference position of the 3D scanner devices when constructing a surface model 112 with respect to the object (e.g. the target portion of the patient 118), according to its own coordinate system. This reference position is therefore selected as the virtual camera position from which the 3D surface model is seen in its own coordinate system, and may be the initial or the final position in the object scanning process, or it may be dynamic and moves with the scanner device (e.g. a time-of-flight camera), or it may be any other alternative position selected by the computer means 100 that processes the 3D scan. In the embodiments, the stereoscopic cameras 201, 202 and the 3D scanner 203 may remain close to each other in a fixed position. This may offer the most precise possible surface reconstruction 112 from the perspective view of the stereoscopic video 116 obtained, and to do the stereoscopic video—3D surface registration 122 with the least effort on the side of computer means 100 of the system, so that registration is quick and user adjustments needed are limited to the minimum.

In embodiments, the 3D scanner 206 is separated from the stereoscopic cameras 201, 202. In embodiments, their relative position is fixed and known, and the same principles described for fixed positioning apply. In embodiments, multiple scanners and/or video cameras are used, or they are mobile, and their relative orientation angle is determined e.g. by IMUs attached to all devices, which show their orientation relative to each other. In embodiments, the stereoscopic camera system 114 is mobile, and the same 3D scanner system 110 functions as markerless optical tracking system, determining the relative position of the cameras forming the stereoscopic camera system 114, if these are in the field of view of the 3D scanner 110.

In embodiments, the 3D scanner system 110 is used in combination with multiple optical markers placed on the stereoscopic camera system 114, for the precise real-time tracking of its location and orientation. Alternatively, or in addition to the 3D scanner system 110, optical tracking means 136 are used for an accurate relative positioning of cameras 114. Optical tracking is made with a tracker camera and markers that locate the 3D scanner devices 110 and stereoscopic cameras 114 in the common coordinate system, which may be based on 3D-2D point correspondences.

In embodiments, the device or devices composing the 3D scanner system 110 include one or more cameras (e.g. time-of-flight cameras). The camera or cameras may form part of the stereoscopic camera system 114. Registration of 3D surface and stereoscopic video 122 is therefore done directly within the coordinate system of the device.

In embodiments, the cameras forming the stereoscopic camera system 114 are used to process a surface reconstruction of the portion of the patient 118, for example using range imaging techniques (e.g. structure-from-motion). That surface reconstruction has a relative position that is determined with respect to the cameras forming the stereoscopic camera system 114. The surface reconstruction may be used for registration 122 with the 3D surface obtained by the 3D scanner system 110, which may reduce the need for other tracking devices.

In embodiments, this surface reconstruction obtained from images of the stereoscopic camera system 114 is used directly for 3D volume—3D surface registration, and this registered image is used for comparison with the 3D volume—3D surface registration 120 made with the surface reconstruction 112, to more precisely define the precise position of the 3D volume in the coordinate system.

In embodiments, once the initial 3D volume—3D surface registration 120 and stereoscopic video—3D surface registration 122 are done, the tracked location and orientation angles of the two-dimensional cameras 114 with respect to the portion of the patient 118 (e.g. tracking the selected anatomic landmarks of the patient 118) are used as the location and orientation parameters for the virtual cameras defined for capturing the 3D volume images. In this manner, 3D volume—stereoscopic video registration is done directly, without an intermediate surface reconstruction 112. This direct 3D volume—stereoscopic video registration is further adjusted through real-time user interface means 132, and it may be combined with other images through image processing 124, according to the different embodiments.

In embodiments, tracking means 136 may include a tracking camera that works in conjunction with active or passive optical markers that are placed in the scene. In embodiments, the tracking camera may be part of the 3D scanner system 110. In embodiments, tracking means 136 include passive or active optical markers that work in conjunction with the tracking camera. Different kinds of tracking systems may be employed, either alone or combined, such as magnetic tracking, inertial tracking, ultrasonic tracking, electromagnetic tracking, etc. Mechanical tracking is possible by fitting the joints of the mechanical arm 204 attached to the ceiling 205 with encoders.

In embodiments, known optical markerless or marker-based tracking systems are used and their data processed 326 by computer means 100 for the tracking of location and/or orientation of the instruments and devices 138, the patient 118, the imaging devices 106, the surgeon 128, and more precisely they are used for image processing 124, e.g. for 3D volume—3D surface registration 120, or for 3D surface—stereoscopic video registration 122, or even for direct registration of 3D volume with stereoscopic video 116, either alone or in combination with the other embodiments described. Such image registration examples involve also interaction of the surgeon 128 or other users with the computer 100, through the available user interface means 130, 132.

In embodiments, the surgeon 128 uses a stereoscopic display 126 and can examine the spatial relationship between the anatomical structures from varying positions. Utilizing the stereoscopic display, the surgeon 128 may not need to look back and forth between monitors and patient 118, and to mentally map the image information to the patient 118. As a consequence, the surgeon 128 can better focus on the surgical task at hand and perform the operation more precisely and confidently.

In embodiments, the display 126 may be a simple stereoscopic video display, or alternatively it may be a stereoscopic virtual reality display, that allows for interaction of the surgeon 128 or other users with the virtual environment created by computer means 100, e.g. through motion tracking and gesture recognition. In embodiments, as shown in FIG. 2, the stereoscopic display 214 is head-mounted 213, and it may include headphones 219 and a microphone, to receive information in audio format and be able to communicate with other users.

In embodiments, the stereoscopic display 126 is composed of a virtual reality device, and the stereoscopic camera system 114 is composed of fixed cameras, or cameras that do not move with the head of the surgeon 128, so that the stereoscopic view displayed to the virtual reality device moves as the head of the surgeon 128 moves, using its own tracking means 136 (e.g. optical marker-based tracking), without the need to change the position of the cameras 114 to change the view. For example, if the stereoscopic camera system 114 obtains a 360° view of the target portion of the patient 118, when the surgeon 128 moves his or her head, that movement is tracked by the head-mounted display 126, changing the perspective view accordingly. Alternatively, the display 126 may not be head-mounted, but e.g. a 3D monitor mounted on an articulated mechanical arm, on a fixed pole, or any other suitable support, either fixed or mobile. Alternatively, the display 126 is a two-dimensional display, and 2D video images 116 are displayed.

The stereoscopic camera system 114 displays a real-time stereoscopic image to the surgeon 128 through the display system 126, which is connected to the computer 100 by wired or wireless (e.g. Bluetooth or Wi-Fi) means, depending on the needs of surgery and on the possibilities of the operating room. Computer means 100 integrate information from the different devices used as described in the different embodiments, and different combinations of stereoscopic video 116, 3D surface, and 3D volume images are shown in a stereoscopic manner to the surgeon 128, with the modifications, additions and deletions as adjusted by the surgeon 128 or other users in real time, so that the surgeon 128 sees the information that he or she wants (from the data available) at any time during the procedure.

In embodiments, the stereoscopic display 126 is a virtual reality device that allows for gesture recognition (e.g. through motion tracking), displaying the real-time user interface means 132 within the field of view of the surgeon 128. Such virtual graphics displayed within the field of view of the surgeon 128 allow for interaction with the computer 100. For example, the surgeon 128 may see virtual buttons in a marginal position of his or her field of view, which may be pressed with a predetermined hand gesture. A virtual button, when pressed, may allow the surgeon 128 e.g. to select a virtual image (e.g. a 3D volume image), and translate and rotate it with his or her hand movements, to adjust its position with respect to the stereoscopic video 116. In embodiments, voice recognition included in the display 126 or in another device connected to the display 126 through computer means 100 allows e.g. to show the virtual graphics (e.g. buttons) only when saying the appropriate word or words, so that virtual graphics for interaction do not interfere with surgery.

In embodiments, the stereoscopic video 116 may be directly sent to the display 126, either by wired or wireless means. Through user interface means 130, 132, the surgeon 128 can select that the stereoscopic video 116 be directly sent to the display 126 after being received by the computer 100. Alternatively, the surgeon 128 may select that the video signal from the stereoscopic cameras 114 be sent directly to the display 126, through a direct wired or wireless connection between both devices. The stereoscopic video images 116 are received by the computer 100 for image processing 124, e.g. for the stereoscopic video—3D surface registration 122. The use of a direct connection between the video 116 (or the cameras 114) and the display 126 makes the time lag negligible for practical purposes during surgery. Integration of the images processed 124 with the real-time stereoscopic video 116 sent directly to the display 126 may allow for real-time user interaction via user interface means 132. For example, the display 126 may show the registered 3D volume blended with the real-time stereoscopic video 116 image directly sent to the stereoscopic display 126, instead of the stereoscopic video image 116 processed 124 by computer means 100. As another example, the display 126 may switch to the images processed 124 by computer means 100 only when the surgeon 128 allows for it, e.g. when more time lag is acceptable.

In an alternate embodiment, a stereoscopic optical see-through display is used as display system 126 from those commercially available (e.g. optical see-through glasses), and real-time images of the patient 118 are directly available to the surgeon's 128 point of view, instead of (or in combination with) the stereoscopic video images 116. The 3D volume blended with the 3D surface is tracked in space to the location and orientation of the stereoscopic display 126, by way of tracking means 136 (e.g. markerless optical tracking and IMU in both devices). Alternatively, the tracked position of the head of the surgeon 128 is used to define the location and orientation of the virtual cameras offering the stereoscopic view (or the virtual camera offering a 2D view) of the 3D volume image. Thus, allowing for an instant registration of the surgeon's 128 direct vision of the portion of the patient 118 and the 3D volume image, that may be adjusted with the available real-time user interface means 132.

In an embodiment, the display system 126 is a projector which projects the processed images 124 over the target portion of the patient 118. In order to achieve a seamless integration with the surgeon's 128 view of the patient 118 during surgery, tracking means 136 are used to accurately track in real time the position of the projector and of the head of the surgeon 128, relative to the common coordinate system. Computer means 100, taking into account the location, orientation and lens-characteristics of the projector, send the blended images that are projected over the patient 118, so that the images appear to the surgeon 128 as a property of the target portion of the patient 118, with the desired adjustments in transparency, color, contrast, etc. In embodiments, the projector projects a stereoscopic view over the patient 118, which is viewed by the surgeon 128 wearing the corresponding glasses, e.g. glasses with polarized filters for a projector that uses a polarization stereoscopic display system (a type of "passive" stereoscopic system).

In embodiments, changes in position of the surgeon's 128 head are tracked with a head-mounted virtual reality or any other stereoscopic display 126 (the preferred stereoscopic video display for this invention, or alternatively the optical see-through display or projector as described), so that the augmented reality view 346 offered to the surgeon 128 changes in real time. In embodiments, to limit the time lag of the stereoscopic video images 116, the virtual graphics provided directly by computer means 100 using tracking 136 and software means are displayed directly to the surgeon's 128 field of view following his or her tracked head position. The virtual graphics are displayed alone, e.g. the registered 3D volume and 3D surface images, hence limiting the time lag effect, and guiding the surgeon 128 in the actual scene that is happening in the operating room. Alternatively, the virtual graphics are sent directly to the display 126, but combined with the available stereoscopic video images 116 (sent directly to the display 126, or after undergoing image processing 124), sacrificing a more precisely blended image in exchange for less time lag with respect to the real scene.

Recording means allow one to record all images received by the computer 100, and the augmented view 346 displayed to the surgeon 128.

In embodiments, the augmented view 346 may comprise a real view blended with virtual graphics. The real view is provided as stereoscopic video images 116 of the scene. The virtual graphics is derived from computer means 100, e.g. 3D volume or digital images 108 of preoperative images 102, generally a CT scan, or an MR scan, or a combination of them. In this case the virtual graphics also correspond to views of real anatomic structures, available to the surgeon 128 only as computer graphics renderings.

The real view of the external structures and the virtual view 346 of the internal structures are blended with the help of a surface reconstruction 112, as already described, and they are shown in-situ with an appropriate degree of transparency, which may vary as the field of view changes. Registration between real and virtual surfaces makes all structures in the augmented view 346 be positioned in the correct location with respect to each other, therefore the derived image of the internal anatomical structure is directly presented in the surgeon's workspace in a registered fashion.

The image display of the 3D volume obtained through volume rendering 104 is the virtual 3D representation of a volume data set as it is "flattened" onto one or more 2D planes. Different techniques are available using software-based and hardware-based solutions that may optimize image accuracy, speed, quality, or a combination of them. Nonlimiting examples of techniques for 3D volume image display include ray casting, fly-through, multiple views, obscured structure, shading depth cues, kinetic and stereo depth cues. Such techniques are available in the computer means 100, and are selected by the surgeon 128 through the available user interface means 130, 132.

According to the embodiments described for surface reconstruction 112, the position of the devices that compose the stereoscopic camera system 114 and/or 3D scanner system 110 is dynamically tracked to display the precise location and orientation of the 3D surface model with respect to the view of each camera 114, which may provide a blended image output 340 to the display 126.

Therefore, when 3D volume—3D surface registration 120 is presented, a stereoscopic view of the 3D volume is presented 342 (either fully automatically by software or with user interaction 350). The 3D volume may take into account the pose changes of the patient 344, and it is displayed to the surgeon 128 according to the precise location of the cameras 114. Accordingly, there may be a seamless integration of all views (e.g. stereoscopic video 116, 3D surface and 3D volume) to both eyes as an augmented view 346 of the surgical field. The same principles apply to all images displayed stereoscopically to the surgeon 128, when fitting the reconstructed 3D surface of the portion of the patient 118, as well as to the different augmented reality helps 346 displayed, such as notifications 348. For example, when using a pair of two-dimensional cameras as the stereoscopic camera system 114, the virtual cameras (that define stereoscopic views of the 3D surface) are positioned by computer means 100 within the common coordinate system to the corresponding position of the two-dimensional cameras (and thus the specific interpupillary distance selected by the surgeon 128), each image being displayed to each corresponding eye of the surgeon 128 by the stereoscopic display 126, together with the corresponding stereoscopic video image 116. The surgeon 128 and other users are able to define or adjust the position of the virtual cameras defining the 3D volume and/or the 3D surface using the available general user interface means 130, and the real-time user interface means 132 during surgery.

In embodiments, the virtual cameras based on the position of the stereoscopic camera system 114 are also used to create views of the 3D volume for registration with the 3D surface, and the stereoscopic view of the registered image is automatically blended with the stereoscopic view of the registered 3D surface—stereoscopic video 122. Alternatively, the virtual cameras defined are used for direct registration with the stereoscopic video 116. Alternatively, the virtual cameras are based on the position of the head of the surgeon 128, and they are used to be shown in the optical see-through display, or alternatively they are projected over the patient 118, according to the different embodiments of the present invention.

Once the initial position of the virtual cameras is determined, computer means 100 translate their location and orientation changes in real time, with data acquired from tracking means 136, e.g. according to the corresponding position of the devices forming the stereoscopic camera system 114. Therefore, the position of the device or devices composing the stereoscopic camera system 114 is tracked, and changes in location and rotation (relative to their initial position during registration) are translated to the position of the corresponding virtual camera or cameras. In this manner, when using a mobile stereoscopic camera system 114, the surgeon 128 sees a direct, seamless view of the inner anatomic structures of the patient 118 blended with the stereoscopic video 116 that defines his or her basic view. As another example, when using tracking data from a head-mounted stereoscopic display 126 (e.g. virtual reality device), changes in its position are translated to the position of the virtual cameras defined, so that the perspective view of the virtual graphics (e.g. the 3D volume) changes to fit the view of the surgeon 128.

In embodiments, especially in settings where preoperative volumetric data is not available, and simple X-ray images and intraoperative fluoroscopic X-ray images are frequently used, a mirror system is used attached to the imaging device (e.g. a C-arm) that obtains intraoperative images 106, making the video optical center of the 3D scanner device 112 (e.g. a time-of-flight camera) or the video camera 114 virtually coincide with the X-ray source. The depth sensor from the 3D scanner device 110 used (e.g. a time-of-flight camera) needs to be adjusted to the distance of X-ray source to the detector, and also to the distance from the mirror. In embodiments, a stereoscopic C-arm is used that contains two X-ray sources and detectors, each source with a video camera 114 or a 3D scanner device 110, or both, attached to them in the described manner. Image registration is done according to the principles of the present invention, whereby the surgeon 128 sees real-time stereoscopic video images 116, and the intraoperative X-ray images (either stereoscopic or not) blended with the video images in its precise location over the patient 118.

In embodiments, the digital images 108 or the 3D volume of preoperative 102 or intraoperative 106 images, after being registered with the stereoscopic video 116 images, are displayed blended with the stereoscopic video 116 by means of classical alpha blending. During alpha blending, the registered digital images or virtual graphics are directly superimposed to the stereoscopic video 116 images, and the surgeon 128 sees the digital image 108 or 3D volume over the visible scene, with the selected transparency level, color adjustments, etc.

In other embodiments, the digital images 108 or the 3D volume of preoperative 102 or intraoperative 106 images, registered with the stereoscopic video 116, are displayed blended with the stereoscopic video 116 by means of real-time background subtraction methods. In real-time background subtraction methods the foreground objects in the video or 3D surface images are detected from the different frames (by using reference frames), and thus a background image or model is obtained. For example, in an embodiment using a time-of-flight camera as 3D scanner system 110, multiple real-time images with color and depth information are obtained, and an algorithm (e.g. random forests) is applied to the pixels. The pixels may be classified to belong to an object class, either foreground objects (including e.g. the surgeon's 128 hands and instruments 138) or the background model (including the patient 118), to obtain a probabilistic output of the objects. These objects are identified as label maps, creating then a pixel-wise alpha map, and then using a mixing look up table (LUT) that associates a specific alpha value to each label pair.

Once the mixing LUT is obtained, higher values are given to surgical instruments 138 and surgeon's 128 hands over the background, giving a better depth perception. As another example, foreground objects are similarly identified and classified from RGB data of stereoscopic video 116 or 3D scanner 112 images, especially metallic, bright, thin- and small-shaped instruments or devices 138 (e.g. drill, clamps or scalpels), which are not well reflecting infrared light. A combination of IR- and RGB-based information is calibrated in advance, according to the tools used and the light conditions, and can be further adjusted in real time through the available user interface means 132.

In embodiments, the 3D surface corresponding to the foreground objects, obtained by the background subtraction methods applied to the 3D surface images, is superimposed to the registered and blended stereoscopic video 116 and 3D volume image, using the virtual camera position of each stereo camera 114 to give a perspective view of the surgeon's 128 hands and instruments 138 corresponding to each eye, giving a more realistic augmented view.

In an embodiment, the identified foreground objects from the stereoscopic video 116 are superimposed over the blended 3D volume—stereoscopic video images. In an embodiment, the precise location of the background model in the common coordinate system is used to superimpose the 3D volume over the background model located on each of the stereoscopic video 116 images, leaving the foreground objects (e.g. surgeon's 128 hands and instruments 138) as the original stereoscopic video, without superimposed images.

These foreground objects can then be adjusted in transparency, color, etc. to permit the surgeon 128 to see the virtual graphics through them, e.g. the internal anatomy of the patient 118 in the registered 3D volume image, or the graphical representation of tracked instruments and devices 138.

In embodiments, markers are placed in the target portion of the patient 208 (the target background model), or the surgeon's 128 hand or instruments 138 (the target foreground objects), or in both locations. These markers are tracked by the tracker camera (e.g. forming part of the 3D scanner system), and help obtain a quicker and more precise position of objects. In embodiments, background subtraction methods make use of hardware or software capabilities (e.g. motion detection) of the 3D scanner devices 110, the 3D display 126, or both, to locate the foreground or moving objects.

In embodiments, to take into account real-time, small adjustments in the moving foreground objects, an area surrounding the foreground objects in the target video image is defined by the user interface means 132. This will adjust for minimal real-time movements of the hand or instruments, leaving the background model bigger or smaller than it actually is, depending on the preferences of the surgeon 128. This defined area can be modified in real time (augmented or diminished) by the surgeon 128 by using the real-time user interface means 134.

In embodiments, a motion controller is used, which can be a different device from those described, or one or more of those used in embodiments, such as the 3D scanner device 110 (e.g. time-of-flight camera) or the stereoscopic display 126 (e.g. virtual reality display), using their own computer-implemented software for gesture recognition. Gesture recognition is used as real-time user interface means 132 e.g. to more accurately adjust the position of the stereoscopic cameras 114, the registration of 3D volume image and stereoscopic video 116, the surface reconstruction 112 (or its parameters), the image processing 124 (e.g. stereoscopic views of the 3D volume and other images), and any other possible software-controlled task of this invention, avoiding the need to touch a device (e.g. mouse or keyboard). For example, when adjusting pose changes 320, gesture recognition may also be used to adjust the position of the different individual bony or soft tissue structures in the 3D volume—3D surface registration 120, in the stereoscopic video—3D surface registration 122, or in any other image processing 124 task. In embodiments, voice recognition is used to interact with the computer 100 through spoken commands, alone or in combination with other computer interface means.

Gesture or voice recognition allows the surgeon 128 to adjust the level of transparency of each superimposed image and their order of visualization; to select the exact layer of the 3D volume image to show; to do with gestures or spoken commands any software-implemented task ideally without touching any device, although other interaction means are available, such as mouse and keyboard. Gesture or voice recognition are activated via a specific gesture, voice command, or by other users, so that it is not active all the time, to avoid real-time interpretation of normal hand movements and normal speech during surgery.

An optional remote user interface allows an additional user to see and interact with the augmented view during the system's real-time operation, as described in this invention. For example, the surgeon 128 may show another person the points to adjust, or tell this person what to change, and this person directly or indirectly interacts with the computer 100 to make the changes, as in the nonlimiting examples of augmented reality described below.

In embodiments, the registered 3D volume image is displayed to the surgeon 128 automatically by layers, e.g. each layer may correspond to the estimated depth that the surgeon's 128 instruments and devices 138 have achieved.

Thus, when dissection is carried out e.g. through the subcutaneous tissue, the superficial layers of the 3D volume image are also automatically made fully transparent, and the deepest layer achieved with the scalpel is shown, or layers above or below the deepest layer are shown with transparency degree as determined by the surgeon 128 through the available interface means 132, to obtain the most intuitive and useful augmented view of the target portion of the patient 118. As another example, only the part of the 3D volume image layer that has been dissected and the selected margin width are made transparent, or other augmented reality modifications are made to them, while the region outside the surgical wound remains in the original state.

In embodiments, the maximum depth achieved by the instruments or devices 138 is obtained by optical tracking from the 3D scanner device 110. For example, depth is estimated from the 3D surface reconstructed 112 according to the device's own coordinate system, in real time (e.g. with a time-of-flight camera). In embodiments, depth calculation is enhanced by using previously made 3D models of the instruments or devices 138, hence more accurately tracking its actual depth and orientation with software-based calculations. In embodiments, depth is calculated by computer means 100 from the stereoscopic video images 116 (e.g. range imaging techniques as in stereo triangulation, or stereophotogrammetric techniques). In embodiments, marker-based optical tracking is used for real-time location and orientation of instruments and devices 138. In embodiments, IMUS attached to the instruments and devices 138 help tracking their real-time orientation. Alternatively, depth is obtained by other tracking means 136 or a combination of them, as described in the different embodiments.

In embodiments, layers of the 3D volume image, blended with the stereoscopic video 116 in the preferred manner, is given a certain percentage of transparency. For example, beginning with 50% for the upper layer (that is the deepest layer achieved e.g. by the scalpel), and being increased following a certain increasing pattern for deeper layers. That way, the surgeon 128 is able to know or more precisely imagine (according to his or her own knowledge) which internal structures may lie ahead and be at risk if dissection is carried out deeper or to the sides of the surgical wound.

In embodiments, intraoperative images 106 (e.g. fluoroscopic images) are displayed directly to the surgeon 128, usually in a marginal position relative to his or her field of view. In embodiments, intraoperative images 106 are tracked to the position of the patient 118 with the help of markerless optical tracking, or alternatively using optical markers (e.g. placed on selected anatomic landmarks of the patient 118, and on the imaging device 106), or by other tracking means 136 or a combination of them, as described in the different embodiments. For example, intraoperative CT scans or MR scans are tracked to the patient 118, or alternatively e.g. with the help of optical markers on the patient 118 and the CT or MR scanner 106, and/or with a tracker camera. As another example, stereoscopic fluoroscopic images taken intraoperatively (either with a specialized image intensifier, or by translating or rotating the image intensifier between images), are shown as a stereoscopic pair of images to the display 126, each image to the corresponding eye of the surgeon 128, either tracked previously to the position of the target portion of patient 118 or not. Alternatively, intraoperative images 106 like fluoroscopic images and CT scans or MR scans are indirectly tracked to the patient 118, automatically by software using the already reconstructed and registered 3D volume—3D surface 120 and 3D surface—stereoscopic video 116, and assisted manually by the surgeon 128 or other users by interaction with the computer 100. Such markerless registration using other precise digital images 108 (e.g. CT scan) or the processed output based on them (e.g. 3D volume image) allows for real-time correction of scale of the fluoroscopic image, either fully automatically or adjusted by interaction of users with the software through the available user interface means 130, 132. In embodiments, tracking means 136 for location and orientation of the intraoperative imaging device 106 (e.g. image intensifier) and the selected anatomic landmarks of the patient 118 give enough data for automated calculation by computer means 100 of the actual size of the imaged structures, so that a precise positioning of the fluoroscopic images is done with e.g. the surface reconstruction 112. The same principles apply to other intraoperative image sources 106, e.g. arthroscopy or ultrasound.

In embodiments, registration of the stereoscopic video 116 is done with a 3D atlas model of the target part of the human body, that consists e.g. of another patient's 3D volume image, or a volume rendering of real anatomic slices (e.g. the Visible Human Project's corresponding male or female dataset), or stereoscopic videos previously recorded (e.g. from similar exposures and surgical techniques), or a 3D virtual anatomic atlas designed in a computer, etc. or a combination of such atlas models. Such registration is done automatically in the most accurate corresponding place over the target portion of the patient 118, according to the principles of this invention, and with help from interaction of the surgeon 128 or other users, either preoperatively or during surgery, e.g. adjusting the size and position of the virtual patient to the real patient 118, the position of their internal structures, etc. using the general user interface means 130. In embodiments, the 3D atlas models are previously processed, e.g. clearly marking important anatomic landmarks and structures at risk, and also differentiating the individual parts and making them movable, to adjust for pose changes in the patient 320, applying the principles of this invention. The registration is also adjusted in real time, as the surgery develops, using the real-time user interface means 132.

In embodiments, only the 3D surface obtained with a 3D scanner 110 is used (without registration with 3D volumetric image of the patient 120), and thus only registration between the 3D surface and the stereoscopic video 122 is done. Measurements of distances and angles are automatically calculated by computer means 100 from the 3D surface model, with or without interaction by the surgeon 118 or other users through the available user interface means 130, 132. For example, the appropriate location and angulation of the tibial cut in a total knee arthroplasty, or the CORA in a proximal tibial osteotomy, are calculated and displayed graphically in real time to the surgeon 118, using e.g. a surface reconstruction 112 of the lower limb or limbs of the patient 118, with or without intraoperative imaging 106, according to the principles of this invention. Measurements and calculations based on the 3D surface may therefore be improved by doing new surface reconstructions 112 when achieving deeper layers of dissection, e.g. when exposing distal femoral and proximal tibial bone during knee arthroplasty, and also when a 3D model atlas (e.g. of a knee) is used for registration of 3D surface—3D model atlas during surgery, according to the principles of the present invention.

In embodiments, optical tracking markers and IMUs are also placed in the selected landmarks of the patient 118, and/or in instruments 138, to offer a more precise positioning of the internal structures of the target portion of the patient 118, for example in cup positioning during total hip arthroplasty. In embodiments, measurements and calculations are made directly over the stereoscopic video 116, with range imaging techniques (e.g. stereo triangulation, or structure-from-motion) or stereophotogrammetric techniques, alone or in combination with the other embodiments.

In embodiments, the registered 3D volume is adjusted during surgery, according to the images taken intraoperatively 106, such as fluoroscopic images. For example, after reduction of fracture fragments, by comparing the newer fluoroscopic images to the previously obtained 3D volume, each fragment individualized in the 3D volume is translated and rotated to the most exact current position, either automatically by computer means 100 (e.g. by computer vision software) or generally with interaction of the surgeon 128 or other users through the real-time user interface means 132.

In an alternate embodiment, intraoperative images 106 (e.g. multiple fluoroscopic projections, stereoscopic or not) are registered with the reconstructed 3D surface. Thus, for example, fluoroscopic images taken intraoperatively are displayed to the surgeon 128 in the corresponding planes with respect to the position of the target portion of the patient 118, blending it with the stereoscopic video 116, and with the preferred transparency, color and contrast values, so that the appropriate entry site location and orientation angle for screw or pin placement is more easily and intuitively determined, e.g. in fractures of the pelvis, after reduction of the fragments, or in scoliosis surgery, for screw positioning.

In embodiments, the general user interface 130 and the real-time user interface 132 allow the surgeon 128 and other users to control the image processing 124 before and during surgery, i.e. to control the augmented reality help 134 sent to the display 126. It allows the surgeon 128 to interactively change the augmented view, e.g. invoking an optical or digital zoom, switching between different degrees of transparency for the blending of real and virtual graphics, show or turn off different graphical structures, etc.

In embodiments, a graphical representation of the instruments and devices 138 used during surgery is available as virtual graphics in the computer 100, and may be selected through the available general user interface means 130, or through the real-time user interface means 132 during surgery. That graphical representation of the instruments and devices 138 is available as a 3D virtual representation (e.g. in STL file format). The 3D virtual representation is obtained directly from the manufacturer; or automatically acquired as a 3D surface by the 3D scanner device 110 (either done before or during surgery), or by software from the video images 116 (e.g. by range imaging techniques); or as a 3D volume rendered 104 from a CT or MR scan data; or as registration of 2D radiographic or fluoroscopic imaging with 3D statistical shape models of similar instruments or devices; or as a simple graphical representation drawn or designed with the known size and shape and added to computer means 100 using the general 130 or real-time user interface means 132.

In embodiments, motion tracking software from the 3D scanner device 110 (e.g. time-of-flight camera) or from the stereoscopic display 126 (e.g. virtual reality device) automatically recognizes the size and shape of the instrument or device 138 used, and automatically selects the corresponding shape and sizes as the virtual graphics for the instrument or device 138. In embodiments, automatic recognition of size and shape of instruments and devices 138 is done by computer means 100 from stereoscopic images taken by the stereoscopic camera system 114 (e.g. by range imaging techniques as stereo triangulation, or stereophotogrammetric techniques), or from stereoscopic radiographic images (e.g. by Roentgen stereophotogrammetry). The real-time location and rotation of the instruments or devices 138 represented as virtual graphics are tracked according to the different embodiments already described, and blending of the virtual graphics with the available images is done using the common coordinate system, through image processing 124 (e.g. with background subtraction techniques) as already described, with interaction from the surgeon 128 and other users.

For example, during percutaneous surgery of e.g. pelvis fracture, when reduction is achieved and a pin is inserted as a guide for the definitive screw, both the pin and the screw have a virtual representation in shape, size, and length, and their rotation and orientation is tracked with the available tracking means 136. Therefore, when the pin or screw enters the inner structures of the body, a graphical representation of a pin or screw with its corresponding shape and size, and with its real-time location and orientation, is displayed to the surgeon 128 in its precise position in the common coordinate system, e.g. blended with the 3D volume image (which is in turn blended with the stereoscopic video 116), according to the principles of this invention, assigning the desired transparency level, color adjustment, etc. In this manner, the surgeon 128 directly sees an intuitive graphical representation of the inner anatomic structures of the target portion of the patient 118, and of the instruments or devices 138 inserted, in their precise real-time position.

In embodiments, the preoperative images 102 and the real-time video images 116 are processed, via classification, to identify structures in the images. Various statistical image-based classification methods allow images of healthy anatomical structures to be distinguished from unhealthy structures (e.g. diseased, malignant, torn/broken/ruptured, etc.), and therefore aid in the identification of conditions by stereoscopic imaging. Functions for performing such classifications may be trained using a training set of image data comprising a variety of different tissue conditions for each anatomical structure of interest to allow conditions of anatomical structures to be distinguished. It will be understood that such processing may occur at the time of image acquisition and storage (e.g. prior to surgery for the preoperative images 102), and/or may be performed at the time of surgery.

In embodiments, image rendering principles and algorithms are applied to the real 2D or stereoscopic video images 116, or to the 3D surface, to detect structures at risk, using color data or texture pattern recognition software, to automatically identify certain structures by their usual color or texture, such as nerves or vessels. They are then displayed by computer means 100 automatically through image processing 124 as determined by the surgeon 128 or other users through available user interface means before 130 or during surgery 132, e.g. in enhanced or different colors (e.g. bright red for arteries), to alert the surgeon 128 of their existence and position. In embodiments, such recognition of structures at risk is done with the help of registration with the 3D volume, e.g. with the previous classification of anatomical structures at risk, either fully automatically through software with statistical image-based classification methods, and/or through interaction of the surgeon 128 or other users with the computer 100, using the available user interface means 130, 132.

In embodiments, markerless motion capture software is used for recognition of moving structures (e.g. vessels), and these structures are displayed by computer means 100 automatically through image processing 124 to the surgeon 128 with a predefined alert notification, e.g. color or contrast change, or showing the suspected (arterial vs. venous) flow, similar to the visual graphics aids shown in Doppler ultrasound. In embodiments, real-time ultrasound or Doppler ultrasound devices are used for identification of structures, blending images according to the principles of this invention (e.g. with tracking of the ultrasound device to the patient 118 and/or to the common coordinate system, and placing the ultrasound images in their corresponding plane), as already described, so that the precise location and orientation of structures is done to the images available through image processing 124.

In embodiments, motion capture software used for human movement recognition is used for skeletal tracking (e.g. with a time-of-flight camera with the appropriate software), and with a previously defined anatomic model (and software for registration of the anatomic model with the 3D volume), each pose change in the patient's 118 skeleton is automatically tracked by software means, and automatic registration of 3D volume—3D surface 120 is done, either as a whole or with anatomic parts individualized, as already described above in the different embodiments.

In embodiments, tracking of joint movement of the patient 118 is used for defining the center of rotation of each joint, and the location and orientation of each joint in their different defining planes. Such information is displayed as numbers and as virtual graphics directly and in real time to the surgeon 128. For example, when applying an articulated elbow external fixator, the most precise center of rotation of the elbow of the patient 118 is identified in real time by the software during surgery, so that the best flexion/extension arc of the elbow is permitted after the surgery.

In embodiments, where color or light changes are used for the identification of internal anatomic structures of the patient 118, as in fluorescence-guided surgery (e.g. 5-ALA PDT in malignant gliomas), even when the eye cannot see the color change under certain circumstances, computer means 100 recognize it from the stereoscopic video 116, and image processing 124 is applied (e.g. changes in color or contrast) to the video image displayed to the surgeon 128, to make such changes visible for the surgeon 128 under the usual light. In this manner, the need to change ambient light and observe fluorescence, change ambient light again to continue the surgery, change light and observe fluorescence again, and so on is avoided. Accordingly, surgical time may be minimized and precision is enhanced.

In embodiments, the computer 100 is connected to an intranet or the Internet, allowing for interactive communication with other people. The augmented view displayed to the surgeon 128 is provided to devices connected to the computer 100, so that the augmented view provided to the surgeon 128 is shared. In this manner, the surgeon 128 and other users (e.g. an observer or associate) may communicate, the other users watching the augmented view on a monitor, stereo monitor, a head-mounted display, or any other 2D or stereo display. For example, the augmented view can be observed by a staff when the resident is operating, or by another expert like a radiologist, pathologist or oncologist. They can perform actions to enter data, such as by way of an interface to the computer 100 (mouse, keyboard, Trackball, etc.) or e.g. through gesture recognition software, certain features to the surgeon 128 by adding extra graphics to the augmented view or highlighting existing graphics that is being displayed as part of the augmented view.

In embodiments, virtual reality headsets are used in combination with a 3D model of the surgeon 128 and/or the other users (e.g. obtained with a 3D scanner), and/or a motion capture device (e.g. time-of-flight camera) pointing at each user interacting with the system, and appropriate software (that e.g. uses a 3D virtual anatomical model of a person with articulated and moveable joints, blending with it the available 3D surface models of the users) to show the users within the field of view of the surgeon 128, and/or the surgeon 128 within the field of view of the users, in real time during surgery, showing their movements, e.g. movements of their hands, for example with real or virtual instruments or devices, over the target portion of the patient 118. In this manner, any user is able to interact directly with the surgeon 128 as a 3D avatar in his field of view in real time during surgery, through the virtual reality display, without the need to share the same room.

In embodiments, a notification system 348 is developed preoperatively. Examples of notifications include, but are not limited to, an alert when approaching certain zones or depth layers (or a location matching both, a zone and a depth layer) of the 3D volume or 3D atlas, to avoid certain important structures at risk of lesion during surgery. Such notifications are output visually to the display 126, audibly via headphones 219 or a speaker in the operating room, or in any other suitable manner. Another example includes that, when the instruments 138 are near those zones or layers, the preferred notification is displayed directly within the surgeon's 128 field of view. The same principle is used to mark the incision lines of the preferred exposures, or trajectory for instruments or devices 138 (e.g. pins or screws), according to previously defined data, similar to a GPS-based auto navigation system.

In another example, information of nearby structures and their distance and precise position is displayed graphically to the surgeon's 128 field of view, according to the automated calculations made by computer means 100, following the principles of the present invention, e.g. while carrying out a dissection, or while reducing a fracture, or positioning an implant. Another example involves using color codes for certain alarms displayed, wherein graphical representations of the instruments or devices 138 used may be turned red when approaching vital structures or when moving away from the desired rotation or location, or green when following the preoperative planning, or when moving closer to the desired rotation or location.

In embodiments, automatic measurements are made and instantly displayed to the surgeon 128 by computer means 100 from the stereoscopic video images 116 or a combination of images taken from some or all of the devices from the stereoscopic camera system 114 and/or 3D scanner system 110, e.g. by range imaging techniques (e.g. structure-from-motion), or stereophotogrammetric techniques. These automatic measurements of portions of the patient 118 and/or instruments and devices 138, may help with accuracy of depth of penetration of instruments or devices 138 into the target portion of the patient 118, or determining the current pose and pose changes of the patient 318, etc. Using the same principles in X-rays, with markerless or marker-based Roentgen stereophotogrammetry (with stereoscopic fluoroscopic images), further adjustments are made for the correct positioning of e.g. instruments and devices 138, or determining patient pose 318, or positioning of fracture fragments reduced during surgery, etc.

In embodiments, preoperative planning done by software means is shown in real time blended with the preoperative 102 and intraoperative images 106 or their graphical representation, e.g. blended with the 3D volume, with the proposed measurements, angles, incisions, osteotomies, etc. drawn and marked. The planning is done and displayed as virtual graphics, either as a 2D drawing or design, or as 3D representation in any of the available file (e.g. STL) or video formats, in stereoscopic manner or not. For example, the appropriate step in surgical technique or guide (from the manufacturer of equipment, or self-made by the surgeon 128 or other users) is shown each time a predefined previous step is completed or skipped (as interpreted automatically by computer means 100, or indicated by the surgeon 128 through real-time interface means 132): graphical representations of the correct or possible instruments and devices 138 are shown, or marked when on the surgeon's 128 field of view; the incorrect ones are marked (e.g. with colors); possible alternative steps and instruments are shown. This intraoperative help includes e.g. any aspect of the surgery or technique, such as plates, screws, sutures, or any other instruments or devices 138, their different sizes, shapes, materials, or a combination of them, available as virtual graphical representations.

In embodiments, augmented reality helps predict the outcome of a procedure. As one example, a virtual model of a flap drawn and displayed stereoscopically blended with the patient's 118 3D surface or 3D volume can be manipulated virtually by the surgeon 128 within his or her field of view, for demonstrating potential outcomes of microsurgery, by adding shape-mapped, scale-mapped, and texture-mapped images blended with the target donor or acceptor portion of the patient 118, or both.

In embodiments, graphical representations (e.g. digital 2D or 3D templates) of instruments and devices 138 (e.g. plates or nails) are displayed stereoscopically and "tried" virtually in real time blended with any of the images displayed to the surgeon 128. For example, once a fracture is reduced or certain steps in surgery have been accomplished, virtual representations of e.g. a plate are virtually tried in the processed images 124 displayed to the surgeon 128 (e.g. blended with the 3D volume and stereoscopic video 116 according to the principles of the present invention), so that the surgeon 128 does not need to try the real plates (or needs to try less plates) over the fracture fragments, hence reducing surgery time and avoiding complications derived from e.g. making a bigger incision, stripping more periosteum for exposure, etc. In embodiments, automated measurements and calculations of instruments and devices 138 are made by computer means 100 and displayed to the surgeon 128 in the same manner. For example, when broaching or reaming bone, or when inserting pins, their estimated depth within bone is automatically calculated, so that measuring of depth with mechanical devices, for estimation of the size of the definitive nail or screw to be inserted, is not necessary.

In embodiments, computer vision algorithms are used for real-time augmented reality help 134. Thus, computer means 100 display directly to the surgeon 128 e.g. which fracture fragments may correspond with which by automatic segmentation software for bone contouring (or e.g. by registration with an image representing the healthy structure, as described above for a fracture involving a hemipelvis), which location and rotation is ideal for arthroplasty or ligament plasties, which layers and borders of the wound correspond with which (to close the wound more precisely), and so forth. As another example, computer vision software helps in classification (as a statistical image-based classification method, as described in the different embodiments above), e.g. detecting soft tissue or bony lesions, by patterns of typical fractures, or patterns of typical tendinous or ligamentous pathology.

In embodiments, 3D volume analysis is done comparing preoperative and intraoperative 3D surfaces obtained from 3D scans of the patient 118, to evaluate for deformity correction during surgery, for example a thorax surface reconstruction is used for pectus excavatum or pectus carinatum correction, cervico-thoraco-lumbo-sacral surface reconstruction is used for scoliosis correction, or pelvic and limb surface reconstruction is used for limb deformity correction.

In embodiments, the stereoscopic camera system 114 has a digital or optical zoom feature that can be utilized during surgery according to the surgeon's 128 needs, to see a magnified augmented view, interacting with the computer 100 through the available user interface means 132. Their precision is enhanced by software (e.g. color, contrast) and external (e.g. light, camera loupes) means as necessary, to more clearly appreciate the anatomy, thus eliminating or reducing the need for other external devices, like surgical loupes or microscopes. The zoom values are also applied to the blended images (e.g. 3D volume, graphical representations) displayed automatically by computer means 100.

In embodiments, the surgeon 128 may input information regarding the condition of the patient 118 for storage with the preoperative images 102. Such information may include, but is not limited to, information related to the diagnosis of the patient 118, and information related to a surgical procedure to be performed on the patient 118. With such information, real-time video images 116 may be compared with the preoperative images 104, 108 or the graphical representation of them (e.g. 3D volume) to determine whether the observed surgical images match expected surgical images based upon the patient condition information. Further, notifications may be generated and output based upon such comparisons. For example, in embodiments, the 3D surface may be compared to such data used to determine whether a surgery is performed on a correct body part or side. As a more specific example, the 3D volume—3D surface registration acquired during surgery may be analyzed to determine that a surgeon 128 is operating on a particular limb of a patient 118, on the correct vertebra or bone within the target portion of the patient 118. Such information may be compared to condition-related information to determine whether the procedure is being performed on the correct limb, target portion or level of the portion of the patient 118.

In embodiments, surgical or technical videos (stereoscopic or not) stored in the computer 100 or streamed from the intranet or Internet may be displayed directly to the surgeon's 128 field of view, blended with the other images displayed, at his or her own discretion (through real-time user interface means 132). Other examples of images that may be displayed include images from surgical atlas, book pages and illustrations, surgical techniques and guides, etc. Therefore, virtually anything available in digital format that helps the surgeon 128 outside the operating room may be displayed in real time during surgery in the surgeon's 128 field of view, according to this invention.

In embodiments, arthroscopy is done with the video images from the arthroscope displayed directly to the surgeon 128 in his own field of view. For example, the images displayed include registered (external) stereoscopic video 116, 3D surface, 3D volume, and other digital images 108, as well as any augmented reality help 134.

In case the arthroscopic imaging is stereoscopic, each image is displayed to the corresponding eye of the surgeon 128 through the stereoscopic display 126. Through tracking means 136 on the arthroscope, the principles of this invention are applied for automated registration of internal (arthroscopic) stereoscopic video with 3D surface, 3D volume, digital images 108, and external stereoscopic video 116. Accordingly, stereoscopic video images of the external surface and internal structures may be displayed, either alone or combined in the surgeon's 128 field of view, registered and blended with the available preoperative 102 or intraoperative 106 images. Augmented view examples include its use to observe how potential stitches (using the available images, such as the 3D volume rendering 104) may interact with other anatomy, and to choose stitch locations based upon such demonstrations. Another example involves the use of image registration and augmented reality help to achieve the best possible position for tibial and femoral tunnels during ligamentoplasty.

In case of ultrasound and ultrasound-guided surgery, ultrasound images may undergo automatic registration and be blended with the other images available, or may be displayed directly to the surgeon's field of view 128. An example includes tracking the ultrasound probe positioning, which is done with any combination of the aforementioned tracking means 136, to allow for an automatic registration of stereoscopic video 116 with the ultrasound images, positioning the ultrasound images on the precise plane over the target portion of the patient 118, with the images displayed as viewed from a virtual camera sharing the location and orientation angles of the stereoscopic camera system 114, blended according to the principles of the present invention.

As examples of robotic feedback, gloves and other hand-wearable devices are used for active motion, and also for passive feeling. In embodiments, "active" wearable gloves are used during surgery, limiting the movement of fingers, hand, and wrist of the surgeon 128, by augmenting resistance, or even completely blocking movement of the joints, when the instruments and devices 138 approach predetermined structures at risk. The computer 100 sends the signal to the gloves to block flexion (and/or extension) of the surgeon's 128 hand and wrist joints when getting closer e.g. to the incision's border or depth planned, the limits of a tumor, when using scalpels, saws, broaches, or any other instrument or device 138, and having a predefined workspace for them, or when approaching structures at risk. As another example, in "passive" hand-wearable devices, computer means 100 interpret e.g. the pressure done by the surgeon's 128 fingers and joints while operating (e.g. while dissecting, or broaching), e.g. with pressure sensors, and compares such pressure with the "normal" pressure in the current and nearby layers (or from statistical pressure range from the different tissues), to determine if the instruments are near to structures at risk, to display alert notifications to the field of view of the surgeon 128, or directly send blocking feedback to the same hand-wearable device with "active" capabilities.

The same principles described above are used in case of a fully automated robotic device, where the surgeon 128 may operate without physically being in the same room as the patient 118.

In embodiments, the principles of this invention are used as a surgical training system, wherein surgery is done over an object, instead of a portion of the real patient 118. For example, to train the surgical skills in spine surgery, the surgeon 128 may operate on an object, e.g. a surgical phantom of a trunk, or the trunk of a cadaver donor, or dead biological tissue with a similar form to a human trunk, or any other suitable object. Registration is done between the available 3D anatomical image (e.g. 3D volume obtained from a CT scan of the trunk of a real patient) and the 3D surface of the real object (e.g. a surgical phantom of a trunk). The 3D volume—3D surface registration 120, and the registration of stereoscopic video—3D surface registration 122 are adjusted before surgery or during surgery by the surgeon 128 or other users through user interface means 130, 132, according to the principles of this invention, to obtain the best possible blending of both structures, the phantom and the preoperative images 102. Alternatively, or in combination with the embodiment above, the 3D surface of the real patient 118 (to whom the preoperative images 102 correspond) is used for an intermediate registration of 3D (phantom) surface—3D (patient) surface, to offer a more precise registration of stereoscopic video 116 and 3D volume. Stereoscopic video 116 is blended with the 3D anatomical images (e.g. the 3D volume, or a 3D anatomic atlas), following the principles of this invention, and the stereoscopic display 126 (e.g. virtual reality display) combined with the different augmented reality helps 134 already described in the different embodiments offer thus an augmented reality environment. In this augmented reality environment, the surgeon 128 is able to perform surgery on objects, while seeing real external and internal anatomic structures. In embodiments, the virtual surgery performed (as seen on the display 126) is recorded in video format, and the virtual stereoscopic result of the surgery is stored as virtual graphics any suitable file format (e.g. STL), whereby the surgeon 128 and other users may study the end result of surgery, e.g. the incision made, the reduction of fracture fragments, the positioning of screws, etc.

In embodiments, the augmented reality training system in accordance to the principles of this invention is used in combination with 3D printing of soft tissues and bone of the target portion of the real patient 118. The 3D printing is based e.g. on the 3D volume obtained from CT and/or MR scans of the patient 118, to obtain a surgical phantom that shares the same shape and size as the real patient 118. The phantom printed includes the structures selected by the user through computer interface means, and these structures are printed in the preferred materials. In this manner, any surgery that has to be done on the real patient 118 may be trained beforehand, according to the principles of this invention, over phantoms that reproduce in detail the target portions of the patient 118. In embodiments, the 3D surface obtained from the real patient 118 is used for image registration with the 3D printed phantom, as already described. In embodiments, phantoms that are 3D printed from real patients are used for training of similar surgical cases, even if the phantom does not exactly correspond to the actual patient 118 that will undergo surgery. The stored video of the surgery, or the stored graphical representation of the end result (e.g. in STL file format), as described above, may thus be used for preoperative planning, for displaying notifications, for identifying structures at risk, etc. to the surgeon 128, during further surgical training on the same or a similar object, or during real surgery to the patient 118, according to the different embodiments described.

In embodiments, the above described methods and processes may be tied to a computing system including one or more computers. Examples of such computing systems may include, but are not limited to, imaging devices 102, 104, computing system 100, 3D scanner system 110, stereo camera system 114, tracking means 136, stereo display 126. In particular, the methods and processes described herein may be implemented as a computer application, computer service, computer API, computer library, and/or other computer program product.

Figure 6:
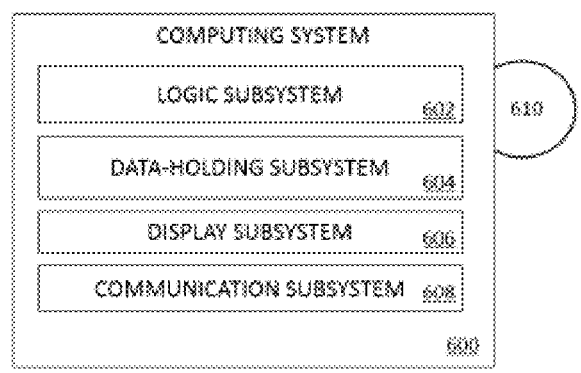
FIG. 6 shows a block diagram depicting a computing device of the present invention.

FIG. 6 schematically shows a nonlimiting computing system 600 that may perform one or more of the above described methods and processes. Computing system 600 is shown in simplified form. It is to be understood that virtually any computer architecture may be used without departing from the scope of this disclosure. In different embodiments, computing system 600 may take the form of a mainframe computer, server computer, desktop computer, laptop computer, tablet computer, home entertainment computer, network computing device, mobile computing device, mobile communication device, gaming device, etc.

Computing system 600 includes a logic subsystem 602 and a data-holding subsystem 604. Computing system 600 may optionally include a display subsystem 606, communication subsystem 608, and/or other components not shown in FIG. 6. Computing system 600 may also optionally include user input devices such as keyboards, mice, game controllers, cameras, microphones, touch screens, gesture and/or voice recognition devices, for example.

Logic subsystem 602 may include one or more physical devices configured to execute one or more instructions. For example, logic subsystem 602 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 602 may include one or more processors that are configured to execute software instructions. Additionally or alternatively, logic subsystem 602 may include one or more hardware or firmware logic machines configured to execute hardware or firmware instructions. Processors of logic subsystem 602 may be single core or multicore, and the programs executed thereon may be configured for parallel or distributed processing. Logic subsystem 602 may optionally include individual components that are distributed throughout two or more devices, which may be remotely located and/or configured for coordinated processing. One or more aspects of logic subsystem 602 may be virtualized and executed by remotely accessible networked computing devices configured in a cloud computing configuration.

Data-holding subsystem 604 may include one or more physical, non-transitory, devices configured to hold data and/or instructions executable by logic subsystem 602 to implement the herein described methods and processes. When such methods and processes are implemented, the state of data-holding subsystem 604 may be transformed (e.g., to hold different data).

Data-holding subsystem 604 may include removable media and/or built-in devices. Data-holding subsystem 604 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 604 may include devices with one or more of the following characteristics: volatile, nonvolatile, dynamic, static, read/write, read-only, random access, sequential access, location addressable, file addressable, and content addressable. In embodiments, logic subsystem 602 and data-holding subsystem 604 may be integrated into one or more common devices, such as an application specific integrated circuit or a system on a chip.

FIG. 6 also shows an aspect of the data-holding subsystem in the form of removable computer-readable storage media 610, which may be used to store and/or transfer data and/or instructions executable to implement the herein described methods and processes. Removable computer-readable storage media 610 may take the form of CDs, DVDs, HD-DVDs, Blu-Ray Discs, EEPROMs, and/or floppy disks, among others.

It is to be appreciated that data-holding subsystem 604 includes one or more physical, non-transitory devices. In contrast, in embodiments aspects of the instructions described herein may be propagated in a transitory fashion by a pure signal (e.g., an electromagnetic signal, an optical signal, etc.) that is not held by a physical device for at least a finite duration. Furthermore, data and/or other forms of information pertaining to the present disclosure may be propagated by a pure signal.

The terms "module," "program," and "engine" may be used to describe an aspect of computing system 600 that is implemented to perform one or more particular functions. In some cases, such a module, program, or engine may be instantiated via logic subsystem 602 executing instructions held by data-holding subsystem 604. It is to be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" are meant to encompass individual or groups of executable files, data files, libraries, drivers, scripts, database records, etc.

It is to be appreciated that a "service," as used herein, may be an application program executable across multiple user sessions and available to one or more system components, programs, and/or other services. In some implementations, a service may run on a server responsive to a request from a client.

When included, display subsystem 606 may be used to present a visual representation of data held by data-holding subsystem 604. As the herein described methods and processes change the data held by the data-holding subsystem, and thus transform the state of the data-holding subsystem, the state of display subsystem 606 may likewise be transformed to visually represent changes in the underlying data. Display subsystem 606 may include one or more display devices utilizing virtually any type of technology. Such display devices may be combined with logic subsystem 602 and/or data-holding subsystem 604 in a shared enclosure, or such display devices may be peripheral display devices.

When included, communication subsystem 608 may be configured to communicatively couple computing system 600 with one or more other computing devices. Communication subsystem 608 may include wired and/or wireless communication devices compatible with one or more different communication protocols. As nonlimiting examples, the communication subsystem may be configured for communication via a wireless telephone network, a wireless local area network, a wired local area network, a wireless wide area network, a wired wide area network, etc. In embodiments, the communication subsystem may allow computing system 600 to send and/or receive messages to and/or from other devices via a network such as the Internet.

In embodiments, the stereoscopic video image 116 is taken as the adaptable basic view of the surgeon 128 or surgeons, and may follow the surgeon's 128 head movements, or be independent of his or her position in the operating room. Digital images and virtual graphics blended with the stereoscopic video 116 enhance the displayed image, and may even substitute it completely, through image processing 124, which may provide a fully customizable view to the surgeon 128.

3D scanner devices 112 described in embodiments may offer an intermediate step for registration between stereoscopic video 116 and the graphical representation (e.g. 3D volume) of a preoperative 102 or intraoperative image 106, which allows for a more accurate, quicker, real-time image registration with automatic patient 118 pose change adaptation, within a simple image-guided navigation system, using the available markerless or marker-based registration methods. The surgeon's 128 viewpoint (the stereoscopic camera system 114) in turn, is independent from the 3D scanner system 112, and can be fixed or dynamic. Accordingly, embodiments may be a more cost effective, in initial investment as well as in fungibles (e.g. markers). Embodiments may make use of anatomical models and volume rendering 104 of individualized parts allowing for a precise registration of pose changes of the patient 118 to the 3D volume 320, by determining pose changes in real time 318 and translating them into a predefined 3D anatomical model with moveable inner structures. Image processing 124 (including the precise blending of the available images) and augmented reality help 134 are adjusted during surgery through real-time user interaction 132 e.g. through gesture recognition (without the need to physically touch interface means), outpacing the current limitations of the available navigation systems.

Tracking of imaging devices 106, patient 118, instruments and devices 138, is done with optical marker-based or markerless means, e.g. with tracker cameras forming part of the 3D scanner system 110. Tracking data is made available as virtual graphics directly into the surgeon's view 128 in a stereoscopic way, offering a direct, precise and intuitive guide for positioning of instruments and devices 138 during surgery. Preoperative 102 and intraoperative images 106 are also displayed directly to the surgeon's 128 field of view, and stereoscopic views offer more accurate representations of the available digital and virtual (e.g. 3D volume) images during surgery. All preoperative 102 and intraoperative images 106 may tracked to the current pose of the patient 118 during surgery, according to the principles of this invention.

With this navigation system there is real-time interaction of the surgeon 128 with software-based tasks through the general 130 or real-time user interface means 134, e.g. by gesture or voice recognition. Gestures are recognized by motion tracking software, e.g. from images by the 3D scanner device 110, or the stereoscopic display 126, or from stereoscopic video images 116. That makes the navigation system even more accurate, with instant adjustments made by the surgeon 128 or other users to image processing 124, e.g. to the registration of images, or to the augmented reality help 134 displayed. Computer means 100 in accordance with this invention, and especially with the stereoscopic display 126, offer a wide range of augmented reality possibilities that are of great help to the surgeon 128 during surgery.

As already described in the embodiments above, stereoscopic video 116 may be sent directly to the display 126, and then undergo registration in the computer 100 being blended with the other images available, making the real time lag between actual scene and stereoscopic video 116 negligible. Also, as already described in the embodiments above, changes in position of the patient 118, instruments and devices 138 and/or surgeon's 128 head are tracked, so that the perspective view of the virtual graphics composing the augmented reality view change in real time. Therefore, images available to computer means 100 (e.g. 3D surface, 3D volume, or virtual representation of instruments or devices 138) may adjust more quickly to changes in the position of the patient 118, instruments or devices 138, or the surgeon's 128 head than registered stereoscopic video (that needs to pass from the cameras 114 to the computer 100 as digital video 116, and then processed 124 for registration), or even than stereoscopic video 116 sent directly to the display 126. When the available digital images (e.g. 3D surface, 3D volume) and virtual graphics are sent directly to the display 126 (once the initial registration of images has been done), without blending with the stereoscopic video 116, the time lag between the real scene and the surgeon's 128 view is still less appreciable.

Other embodiments may be utilized in combination with an optical see-through display, tracking the surgeon's 128 head, using any of the commercially available devices for this task (e.g. optical see-through glasses). Alternatively, a stereoscopic display 126 is used that works as a video see-through device during the surgery, but turns into an optical see-through display, thanks to the percentage of transparency applied to the display's special glasses. Alternatively, a projector is used that projects the processed images 124 directly to the target portion of the patient 118. Alternatively, the surgeon 128 may ask for a change of display during surgery, having them both head-mounted, or being helped by another member of the surgical team who changes them, whenever the surgeon 128 feels the need for a lag-less vision.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:
1. A system comprising:
a stereoscopic optical see-through head mounted display;
a physical instrument or physical device;
at least one computing system; and
at least one camera,
  wherein the at least one computing system is configured to track, using the at least one camera, a first marker configured to be attached to a bony structure of a physical spine of a patient and a second marker configured to be attached to the physical instrument or the physical device,
  wherein the at least one computing system is configured to generate a three-dimensional (3D) surface representation of at least a portion of the tracked physical instrument or physical device,
  wherein the at least one computing system is configured to generate a 3D stereoscopic view, displayed by the stereoscopic optical see-through head mounted display, the 3D stereoscopic view comprising the 3D surface representation of the at least portion of the tracked physical instrument or physical device,
  wherein the system is configured to adjust in real time the 3D stereoscopic view responsive to movement of the stereoscopic optical see-through head mounted display, wherein the system is configured to adjust in real time the 3D stereoscopic view responsive to movement of the physical spine from a first position to a second position, wherein the at least one computing system is configured to superimpose the 3D stereoscopic view on a target portion of the physical spine, and wherein the first and second positions of the physical spine of the patient are different.

2. The system of claim 1, wherein the at least one camera is head mounted with the stereoscopic optical see-through head mounted display.

3. The system of claim 1, wherein the at least one camera is separate from the stereoscopic optical see-through head mounted display.

4. The system of claim 1, wherein the computing system is configured to update the location and orientation of the 3D surface representation in real-time in the stereoscopic optical see-through head mounted display.

5. The system of claim 1, wherein the 3D surface representation of the at least a portion of the tracked physical instrument or physical device comprises a virtual trajectory for the physical instrument or physical device, a virtual pin, a virtual screw, a virtual nail, a virtual plate, a virtual template of the physical instrument, a virtual template of the physical device, or any combinations of the foregoing.

6. The system of claim 1, wherein the position and orientation of the 3D surface representation of the at least portion of the tracked physical instrument or physical device is updated in real time based on the position and orientation of the second marker.

7. The system of claim 1, wherein the system further comprises at least one inertial measurement unit, wherein the at least one inertial measurement unit is attached to the at least one of the camera, the stereoscopic optical see-through head mounted display, the physical instrument, the physical device, a surgeon, or a 3D scanner system.

8. The system of claim 1, wherein the first marker comprises at least one optical marker and at least one radiopaque marker.

9. The system of claim 8, wherein the at least one radiopaque marker is included in an image information of the physical spine of the patient, wherein the image information comprises at least one of preoperative, intraoperative, or preoperative and intraoperative image information of the physical spine.

10. The system of claim 9, wherein the at least one computing system is configured to register the image information with the physical spine using the at least one radiopaque marker.

11. The system of claim 8, wherein the optical marker is a color marker, a reflective marker, or a color marker and a reflective marker.

12. The system of claim 1, wherein the 3D stereoscopic view comprises a 3D surface representation of an anatomical model, an image information of the physical spine of the patient, anatomic data derived from an image information of the physical spine of the patient or a combination thereof.

13. The system of claim 12, wherein the at least one computing system is configured to generate the 3D surface representation of the anatomical model, the image information of the physical spine of the patient, the anatomic data derived from the image information of the physical spine of the patient or the combination thereof based on at least one 2D image, at least one 3D image, or at least one 2D and at least one 3D image of the physical spine, wherein the at least one 2D image, at least one 3D image or combination thereof comprises a CT image, an MRI image, an ultrasound image, an x-ray image or combinations thereof.

14. The system of claim 1, wherein the first marker comprises two or more markers configured to be attached to a bony structure of the physical spine of the patient, or wherein the second marker comprises two or more markers configured to be attached to the physical instrument or the physical device, or wherein the first marker comprises two or more markers configured to be attached to a bony structure of the physical spine of the patient and wherein the second marker comprises two or more markers configured to be attached to the physical instrument or the physical device.

15. The system of claim 1, wherein the at least one computing system is configured to determine in real time the relative location, orientation or location and orientation of the physical instrument or the physical device, the first marker, the second marker, the physical spine, a surgeon, the stereoscopic optical see-through head mounted display, or any combinations of the foregoing.

16. The system of claim 1, wherein the at least one computing system comprises the computing system configured to track, using the at least one camera, the first marker configured to be attached to the bony structure of the physical spine and the second marker configured to be attached to the physical instrument or the physical device, the computing system configured to generate the 3D surface representation of the at least portion of the tracked physical instrument or physical device, the computing system configured to generate the 3D stereoscopic view, displayed by the stereoscopic optical see-through head mounted display, the computing system configured to superimpose the 3D stereoscopic view on the target portion of the physical spine, and wherein one or more of the at least one computing system are the same.

17. The system of claim 1, wherein the at least one computing system comprises the computing system configured to track, using the at least one camera, the first marker configured to be attached to the bony structure of the physical spine and the second marker configured to be attached to the physical instrument or the physical device, the computing system configured to generate the 3D surface representation of the at least portion of the tracked physical instrument or physical device, the computing system configured to generate the 3D stereoscopic view, displayed by the stereoscopic optical see-through head mounted display, the computing system configured to superimpose the 3D stereoscopic view on the target portion of the physical spine, and wherein one or more of the at least one computing system are different.

18. The system of claim 1, wherein the at least one computing system is configured to provide for adjustment of transparency, color, contrast or combinations thereof of the 3D stereoscopic view displayed by the stereoscopic optical see-through head mounted display superimposed on the target portion of the physical spine.

19. The system of claim 12, wherein the 3D surface representation of the anatomical model, the image information of the physical spine of the patient, the anatomic data derived from the image information of the physical spine of the patient or the combination thereof comprises a 3D surface representation of one or more individualized vertebrae.

20. The system of claim 1, comprising at least one passive optical marker, active optical marker, inertial measurement unit, magnetic tracking device, electromagnetic tracking device, ultrasonic tracking device, mechanical tracking device, tracking device using inertial measurement units, 3D scanner, camera, navigation system or a combination thereof configured to track the physical instrument or the physical device, the physical spine, a surgeon, the optical see-through head mounted display or a combination thereof.

21. The system of claim 1, wherein the movement from the first position to the second position of the physical spine during surgery is a rotation or a lateralization of at least one vertebrae.

22. The system of claim 1, wherein the at least one computing system is configured to obtain coordinate information of the physical instrument or the physical device, the first marker, the second marker, the physical spine, a surgeon, the stereoscopic optical see-through head mounted display or a combination thereof in a coordinate system.

23. The system of claim 22, wherein the coordinate system is the coordinate system of the at least one camera.

24. The system of claim 22, wherein the coordinate system is the coordinate system of the first marker.

25. The system of claim 1, wherein the at least one camera is configured to use visible light information.

26. The system of claim 1, wherein the at least one camera is configured to use infrared light information.

27. The system of claim 1, wherein the system is configured to generate the 3D surface representation of the at least portion of the tracked physical instrument or physical device from at least one point cloud, mesh, or a combination thereof.

28. The system of claim 7, wherein the computing system is configured to adjust in real time the at least one 3D stereoscopic view responsive to movement of the stereoscopic optical see-through head mounted display using the at least one an inertial measurement unit.

29. The system of claim 1, further comprising a 3D scanner, a video system or a 3D scanner and a video system configured to track the movement from the first position to the second position of the physical spine.

30. The system of claim 1, wherein the target portion of the physical spine is a process, pedicle, lamina or posterior body of a vertebra.

* * * * *